United States Patent [19]

Eichenberger et al.

[11] Patent Number: 4,808,603
[45] Date of Patent: Feb. 28, 1989

[54] 3,5-DIACYL-2,6-DIALKYL-4-ARYL-1,4-DIHYDROPYRIDINES, THEIR USE, AND PHARMACEUTICAL COMPOSITIONS THEREOF

[75] Inventors: Kurt Eichenberger, Therwil; Hans Kühnis, Basel, both of Switzerland

[73] Assignee: Ciba-Geigy Corporation, Ardsley, N.Y.

[21] Appl. No.: 895,604

[22] Filed: Aug. 7, 1986

[30] Foreign Application Priority Data

Aug. 14, 1985 [CH] Switzerland ............... 3504/85

[51] Int. Cl.⁴ ............... C07D 213/55; A61K 31/44
[52] U.S. Cl. ............... 514/356; 546/271; 546/272; 546/273; 546/274; 546/275; 546/276; 546/278; 546/283; 546/284; 546/139; 546/152; 546/321
[58] Field of Search ............... 546/321; 514/356

[56] References Cited
PUBLICATIONS

CA. 97:92145e, 1,4-Dihydropyridine-3,5-Dicarboxylicester Derivatives, p. 758 (1982).
CA. 98:107166j, 1,4-Dihydro-3,5-Pyridinedicarboxylate Esters and Their Salts, p. 589 (1983).
CA. 98:125898d, 1,4-Dihydropyridine-3,5-Dicarboxylic Acid Diesters, p. 622 (1983).
CA. 103:22595v, 1,4-Dihydropyridine Derivatives and Pharmaceutical Compositions Containing Them, p. 579 (1985).
CA. 103:171885s, Calcium Channels: Basic Properties as Revealed by Radioligand Binding Studies, p. 65 (1985).
CA. 103:196015w, Dihydropyridine Compounds and Pharmaceutical Compositions Containing Them, p. 671 (1985).
CA. 104:19517m, Dihydropyridine Derivatives and Their Salts, p. 477 (1986).
CA. 104:88442v, Asymmetrical Diesters of 1,4-Dihydro-2,6-Dimethyl-Pyridine-3,5-Dicarboxylic Acid, p. 648 (1986).
CA. 104:88444x, Dihydropyridine Derivatives, p. 648 (1986).
CA. 104:109644e, 1,4-Dihydropyridine Derivatives and Their Salts, p. 728 (1986).
CA. 104:207171t, Esters of 1,4-Dihydro-2,6-Dimethyl-3-(Alkoxycarbonyl or Alkoxyalkoxycarbonyl)-4-(Substituted Phenylpyridine-5-Carboxylic Acid, p. 745 (1986).

Primary Examiner—Alan L. Rotman
Attorney, Agent, or Firm—Irving M. Fishman; JoAnn Villamizar

[57] ABSTRACT

Compounds of the formula

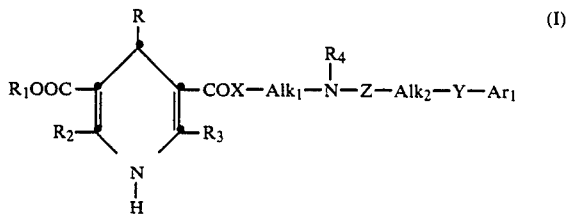

in which R represents a carbocyclic or heterocyclic aryl radical, $R_1$ represents lower alkyl, one of the groups $R_2$ and $R_3$ represents lower alkyl and the other represents lower alkyl, cyano aor amino, X represents oxygen or the group —NH—, $Alk_1$ represents lower alkylene or optionally substituted phenyl-lower alkylene, which separates the group X from the nitrogen atom by at least two carbon atoms, $R_4$ represents hydrogen, lower alkyl or optionally substituted phenyl-lower alkyl, Z represents the group —(C=O)— or a single bond, $Alk_2$ represents lower alkylene which separates the groups Z and Y preferably by from 2 to 4 carbon atoms, Y represents the group —(C=O)— and $Ar_1$ represents a monocyclic, carbocyclic or heterocyclic aryl radical, and salts of such compounds having salt-forming properties, have cardiovascular properties, especially coronary dilatory and anti-hypertensive properties.

19 Claims, No Drawings

3,5-DIACYL-2,6-DIALKYL-4-ARYL-1,4-DIHYDROPYRIDINES, THEIR USE, AND PHARMACEUTICAL COMPOSITIONS THEREOF

The invention relates to novel unsaturated compounds and salts thereof, processes for their manufacture, pharmaceutical preparations containing these compounds and the use thereof.

The invention relates to compounds of the formula

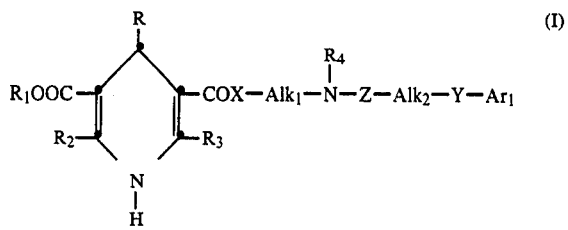

(I)

in which R represents a carbocyclic or heterocyclic aryl radical, $R_1$ represents lower alkyl, one of the groups $R_2$ and $R_3$ represents lower alkyl and the other represents lower alkyl, cyano or amino, X represents oxygen or the group —NH—, $Alk_1$ represents lower alkylene or optionally substituted phenyl-lower alkylene, which separates the group X from the nitrogen atom by at least two carbon atoms, $R_4$ represents hydrogen, lower alkyl or optionally substituted phenyl-lower alkyl, Z represents the group —(C=O)— or a single bond, $Alk_2$ represents lower alkylene which separates the groups Z and Y preferably by from 2 to 4 carbon atoms, Y represents the group —(C=O)— and $Ar_1$ represents a monocyclic carbocyclic or heterocyclic aryl radical, and to salts of compounds of the formula I having salt-forming groups.

A carbocyclic or heterocyclic aryl radical R is especially a corresponding monocyclic radical, but can also be a bi- or poly-cyclic carbocyclic or heterocyclic radical having aromatic properties.

Carbocyclic radicals R of this kind are especially optionally substituted phenyl, and also naphthyl.

Heterocyclic aryl radicals R are preferably corresponding monocyclic radicals, but can also be corresponding bi- or poly-cyclic radicals, it being possible for the latter to consist of several heterocyclic rings, or of one or more heterocyclic rings with one or more fused carbocyclic rings, especially one or more fused benzo rings. The heterocyclic radicals R customarily present, which preferably consist of five or six ring members, may contain as rings members up to four identical or different hetero atoms, especially nitrogen, oxygen and/or sulphur atoms, preferably one, two, three of four nitrogen atoms, an oxygen or sulphur atom, or one or two nitrogen atoms together with an oxygen or sulphur atom. They are customarily bonded via a ring carbon atom to the carbon atom in the 4-position of the 1,4-dihydropyridine ring.

Monocyclic five-membered heteroaryl radicals R are, for example, corresponding monoaza-, diaza-, triaza-, tetraza-, monooxa-, monothia-, oxaza-, oxadiaza-, thiaza- or thiadiaza-cyclic radicals, such as pyrryl, pyrazolyl, imidazolyl, triazolyl, tetrazolyl, furyl, thienyl, isoxazolyl, oxazolyl, oxadiazolyl, isothiazolyl, thiazolyl or thiadiazolyl radicals, whilst monocyclic six-membered heteroaryl radicals R are, for example, corresponding monoaza-, diaza- or triaza-cyclic radicals, such as pyridyl, pyridazinyl, pyrimidinyl, pyrazinyl or triazinyl radicals. Bicyclic heteroaryl radicals are especially monocyclic heteroaryl radicals with a fused benzo ring; the hetero ring may be five- or six-membered, a five-membered heteroaryl radical being, for example, a monoaza-, diaza-, diaza-monooxa-, monooxa-, monothia-oxaza- or thiaza-cyclic radical, and a six-membered heteroaryl radical being, for example, a monoaza- or a diaza-cyclic heteroaryl radical. Such bicyclic radicals that may be bonded via a ring carbon atom of the hetero- or carbo-cyclic radical are, for example, indolyl, isoindolyl, benzimidazolyl, benzoxadiazolyl, benzofuranyl, benzofurazanyl, benzothienyl, benzthiazolyl, benzthiadiazolyl, quinolinyl or isoquinolinyl radicals, it being possible for nitrogen-containing mono- or bi-cyclic heteroaryl radicals of the type mentioned, especially unsubstituted or substituted pyridyl radicals, also to be in the form of N-oxides, for example pyridyl-N-oxide.

A monocyclic carbocyclic aryl radical $Ar_1$ is especially an unsubstituted or mono- or polysubstituted phenyl radical, whilst a monocyclic heteroaryl radical $Ar_1$ is, for example, a monocyclic monooxa-, monoaza- or monothia-aryl radical, for example one such as is defined for R, especially unsubstituted or mono- or poly-, identically or differently, substituted furyl, pyridyl or thienyl.

The carbocyclic and heterocyclic aryl radicals R and $Ar_1$ may be unsubstituted or substituted. Substituents are bonded especially to ring carbon atoms, but also to ring nitrogen atoms. From one to three identical or different substituents may be present, but preferably only one is present. Substituents of ring carbon atoms are, inter alia, optionally substituted hydrocarbon radicals, such as corresponding aliphatic, cycloaliphatic, aromatic or araliphatic hydrocarbon radicals, for example lower alkyl, lower alkenyl, lower alkynyl, lower alkylene, cycloalkyl, cycloalkyl-lower alkyl, phenyl or phenyl-lower alkyl. Substituents of such hydrocarbon radicals, especially of lower alkyl, phenyl or phenyl-lower alkyl are, for example, optionally etherified or esterified hydroxy groups, such as hydroxy, lower alkoxy optionally substituted, for example, by optionally etherified or esterified hydroxy, for example lower alkoxy, lower alkoxy-lower alkoxy or halo-lower alkoxy, lower alkenyloxy optionally substituted, for example, by optionally etherified or esterified hydroxy, for example lower alkenyloxy or halo-lower alkenyloxy, lower alkynyloxy, lower alkylenedioxy, lower alkanoyloxy or halogen, and/or optionally functionally modified carboxy, such as carboxy, esterified carboxy, for example lower alkoxycarbonyl, amidated carboxy, such as carbamoyl, N-lower alkyl-carbamoyl or N,N-di-lower alkyl-carbamoyl, or cyano. Cyclic substituents, especially phenyl, may in addition also contain as substituent(s) lower alkyl, which may optionally be substituted, for example as indicated. Other substituents of aryl radicals R and $Ar_1$ are, for example, optionally etherified or esterified hydroxy groups, such as hydroxy, lower alkoxy optionally substituted, for example, by optionally etherified or esterified hydroxy, for example lower alkoxy, lower alkoxy-lower alkoxy or halo-lower alkoxy, lower alkenyloxy optionally substituted, for example, by optionally etherified or esterified hydroxy, for example lower alkenyloxy or halo-lower alkenyloxy, lower alkynyloxy, lower alkylenedioxy, lower alkanoyloxy or halogen, nitro, optionally substituted amino, such as amino, N-lower alkylamino, N,N- di-lower alkylamino, N-lower-alkyl-N-phenyl-lower alkylamino, lower alkyleneamino, oxa-lower alkyleneamino, thia-lower alkyleneamino or aza-lower alkyleneamino in which the aza nitrogen atom may be unsubstituted or substituted, for example by lower alkyl, phenyl or phenyl-lower alkyl, each optionally substituted, for example as described above, or acylamino, for example lower alkanoylamino, azido, acyl, such as lower alkanoyl or optionally funcionally modified carboxy, such as carboxy, esterified carboxy, for example lower alkoxycarbonyl, or amidated carboxy, such as carbamoyl, N-lower alkyl-carbamoyl or N,N-di-lower alkyl-carbamoyl, also cyano, optionally functionally modified sulpho, such as sulpho, aminosulphonyl, N-lower alkylaminosulphonyl or N,N-di-lower alkylaminosulphonyl and/or etherified mercapto, which may optionally be oxidised, such as lower alkylthio, lower alkylsulphinyl or lower alkylsulphonyl. Substituents of ring nitrogen atoms are especially the above-mentioned optionally substituted hydrocarbon radicals, such as lower alkyl, and also hydroxy or oxido.

Heterocyclic aryl radicals R and $Ar_1$ may, for example depending on the nature of the substitution, be in various tautomeric forms.

The definitions used hereinbefore and hereinafter, unless specifically defined, have the following meanings:

The term "lower" indicates that correspondingly defined groups or compounds, unless defined otherwise, contain up to and including 7, preferably up to and including 4, carbon atoms.

Substituted radicals may contain one or more identical or different substituents; these may occupy any suitable position.

Naphthyl may be 1- or 2-naphthyl.

Pyrryl is, for example, 2- or 3-pyrryl, pyrazolyl is, for example, 3- or 4-pyrazolyl, imidazolyl is, for example, 2- or 4-imidazolyl, triazolyl is, for example, 1,3,5-1H-triazol-2-yl or 1,3,4-triazol-2-yl, and tetrazolyl is, for example, 1,2,3,4-1H-tetrazol-5-yl, whilst furyl is 2- or 3-furyl and thienyl is 2- or 3-thienyl. Isoxazolyl is, for example, 3-isoxazolyl, oxazolyl is, for example, 2- or 4-oxazolyl, oxadiazolyl is, for example, 1,3,4-oxadiazol-2-yl, thiazolyl is, for example, 4-thiazolyl, and thiadiazolyl is, for example, 1,3,4-thiadiazol-2-yl.

Pyridyl is 2-, 3- or 4-pyridyl, pyridazinyl is, for example, 3-pyridazinyl, pyrimidinyl is 2-, 4- or 5-pyrimidinyl, pyrazinyl is 2-pyrazinyl and triazinyl is, for example, 1,3,5-triazin-2-yl.

Indolyl is, for example, 2-, 3- or 5-indolyl, isoindolyl is, for example, 1-isoindolyl, benzimidazolyl is, for example, 2- or 5-benzimidazolyl, benzofuranyl is, for example, 2- or 3-benzofuranyl, benzofurazanyl (also 2,1,3-benzoxadiazolyl) is, for example, 4-benzofurazanyl, benzothienyl is, for example, 3-benzothienyl, benzothiazolyl is, for example, 2-benzthiazolyl, 2,1,3-benzthiadiazol-4-yl, quinolinyl is, for example, 2- or 4-quinolinyl, and isoquinolinyl is, for example, 1-isoquinolinyl.

Lower alkyl is, for example, methyl, ethyl, n-propyl, isopropyl, n-butyl, isobutyl or tert.-butyl, also n-pentyl, n-hexyl or n-heptyl, whilst lower alkenyl is, for example, allyl or methallyl, and lower alkynyl is, for example, propargyl.

Cycloalkyl has preferably from 5 to 7 ring carbon atoms and is, for example, cyclopentyl or cyclohexyl, whilst cycloalkyl-lower alkyl may be, for example, cyclopropylmethyl, cyclopentylmethyl or cyclohexylmethyl.

Phenyl-lower alkyl is, for example, benzyl or 1- or 2-phenylethyl, wherein substituents, especially of the phenyl moiety, are optionally etherified or esterified hydroxy groups, such as hydroxy or halogen, or lower alkyl or lower alkoxy each optionally substituted, for example, by optionally etherified or esterified hydroxy, for example lower alkyl, hydroxy-lower alkyl, halo-lower alkyl, lower alkoxy, lower alkoxy-lower alkoxy or halo-lower alkoxy.

Lower alkoxy is especially methoxy, ethoxy, n-propoxy, isopropoxy, n-butoxy, isobutoxy or tert.-butoxy.

In a lower alkoxy-lower alkoxy radical the terminal lower alkoxy group is separated from the linking oxygen atom preferably by more than one carbon atom; such radicals are, for example, 2-methoxyethoxy or 2-ethoxyethoxy.

In a halo-lower alkoxy radical there may be present one or more halogen atoms that preferably have an atomic number of up to 35 and are especially fluorine and/or chlorine; such radicals are, for example, difluoromethoxy or 1,1,2-trifluoro-2-chloroethoxy.

Lower alkenyloxy is, for example, allyloxy or methallyloxy, and halo-lower alkenyloxy, which may contain one or more halogen atoms, the latter preferably having an atomic number of up to 35 and being especially fluorine and/or chlorine, is, for example, 1,2-dichlorovinyloxy.

Lower alkynyloxy is, for example, propargyloxy, whilst lower alkylenedioxy is, for example, methylenedioxy or ethylenedioxy.

Lower alkylene $Alk_1$ and $Alk_2$ each has up to 8 carbon atoms, and $Alk_1$ separates the group X and the nitrogen atom by from 2 to 8, preferably by from 2 to 4, carbon atoms. Lower alkylene $Alk_2$ separates the groups Z and Y by from 2 to 6, preferably by from 2 to 4, carbon atoms. The two radicals $Alk_1$ and $Alk_2$ are each, for example, ethylene, 1,2- or 1,3-propylene, 1,4-butylene, 1,5-pentylene, 1,6-hexylene, 1,7-heptylene or 1,8-octylene.

Optionally substituted phenyl-lower alkylene $Alk_1$ has in the alkylene moiety likewise up to 8 carbon atoms and separates the group X and the nitrogen atom by from 2 to 8, preferably by from 2 to 4, carbon atoms. Representatives of these radicals $Alk_1$ are, for example, 1-phenyl-1,2-ethylene, 2-phenylethylene or 1- or 2-phenyl-1,3-propylene.

Lower alkylenedioxy is, for example, methylenedioxy or 1,2-ethylenedioxy.

Lower alkanoyloxy is, for example, acetoxy, propionyloxy or pivaloyloxy.

Halogen preferably has an atomic number of up to and including 35 and is especially fluorine or chlorine, also bromine, but can also be iodine.

Hydroxy-substituted lower alkyl is, for example, 2-hydroxyethyl.

Halo-substituted lower alkyl is, for example, trifluoromethyl, 1,1,2-trifluoro-2-chloroethyl or chloromethyl.

Lower alkoxycarbonyl is, for example, methoxycarbonyl, ethoxycarbonyl, n-propoxycarbonyl, isopropoxycarbonyl, n-butoxycarbonyl, isobutoxycarbonyl or tert.-butoxycarbonyl.

N-lower alkyl-carbamoyl is, for example, N-methylcarbamoyl or N-ethyl-carbamoyl, whilst N,N-di-lower alkyl-carbamoyl is, for example, N,N-dimethyl-carbamoyl or N,N-diethyl-carbamoyl.

N-lower alkylamino is, for example, N-methylamino, N-ethylamino, N-n-propylamino or N-isopropylamino.

N,N-di-lower alkylamino is, for example N,N-dimethylamino, N-ethyl-N-methylamino or N,N-diethylamino, whilst N-lower alkyl-N-phenyl-lower alkylamino is, for example, N-benzyl-N-methylamino or N-methyl-N-(2-phenylethyl)-amino.

Lower alkyleneamino preferably contains from 4 to 6 ring carbons atoms and is, for example, pyrrolidino or piperidino, whilst oxa-lower alkyleneamino may be, for example, 4-morpholino, thia-lower alkyleneamino may be, for example, 4-thiomorpholino, and optionally aza-substituted aza-lower alkyleneamino may be, for example, piperazino, 4-methylpiperazino, 4-phenylpiperazino, 4-benzylpiperazino or 4-(2-phenylethyl)-piperazino.

Lower alkanoylamino is, for example, acetylamino or propionylamino.

Lower alkanoyl is, for example, formyl, acetyl, propionyl or pivaloyl.

Lower alkylthio is, for example, methylthio, ethylthio, n-propylthio or isopropylthio, whilst lower alkylsulphinyl is, for example, methylsulphinyl, and lower alkylsulphonyl is, for example, methylsulphonyl or ethylsulphonyl.

N-lower alkylaminosulphonyl is, for example, N-methylaminosulphonyl, whilst N,N-di-lower alkylaminosulphonyl sulphonyl is, for example, N,N-dimethylaminosulphonyl.

In a substituted lower alkoxycarbonyl radical, the substituent is separated from the oxygen atom customarily by at least 2, but preferably by 2 or 3, carbon atoms. Such radicals are, for example, hydroxy-lower alkoxycarbonyl, such as 2-hydroxyethoxycarbonyl or 2,3-dihydroxypropoxycarbonyl, lower alkoxy-lower alkoxycarbonyl, for example 2-methoxyethoxycarbonyl, di-lower alkylamino-lower alkoxycarbonyl, for example 2-dmethylaminoethoxycarbonyl, 2-diethylaminoethoxycarbonyl or 3-dimethylaminopropoxycarbonyl, lower alkyleneamino-lower alkoxycarbonyl, for example -2pyrrolidinoethoxycarbonyl or 2-piperidinoethoxycarbonyl, morpholino-lower alkoxycarbonyl, for example 2-(4-morpholino)-ethoxycarbonyl, or (4-lower alkylpiperazino)-lower alkoxycarbonyl, for example 2-(4-methylpiperazino)-ethoxycarbonyl.

Phenyl-lower alkoxycarbonyl is, for example, benzyloxycarbonyl or 2-phenylethoxycarbonyl.

N,N-lower alkylene-carbamoyl is, for example, pyrrolidinocarbonyl or piperidinocarbonyl, and corresponding radicals in which the lower alkylene moiety is interrupted by oxygen, sulphur or unsubstituted or substituted nitrogen are, for example, 4-morpholinocarbonyl, 4-thiomorpholinocarbonyl, 1-piperazinocarbonyl or 4-methyl-1-piperazinocarbonyl.

Compounds of the formula I having salt-forming basic properties may be in the form of salts, especially acid addition salts, more especially corresponding pharmaceutically acceptable non-toxic acid addition salts. Such salts are, for example, those with mineral acids, such as hydrohalic acids, for example hydrochloric acid or hydrobromic acid, also nitric acid, sulphuric acid or phosphoric acid, or organic acids, such as carboxylic acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-amino-salicylic acid, 2-phenoxybenzoic acid, 2-acetoxybenzoic acid, embonic acid, nicotinic acid or isonicotinic acid, also amino acids, or organic sulphonic acids, such as lower alkanesulphonic acids that optionally contain hydroxy, for example methanesulphonic acid, ethanesulphonic acid, 2-hydroxyethanesulphonic acid or ethane-1,2-disulphonic acid, or arylsulphonic acids, for example benzenesulphonic acid, 4-methylbenzenesulphonic acid or naphthalene-2-sulphonic acid, or with other acidic organic substances, such as ascorbic acid.

Salts of starting materials having salt-forming basic properties are, for example, those with mineral acids, for example hydrochloric acid, sulphuric acid or phosphoric acid, or with organic acids, for example acetic acid.

The compounds of the formula I and salts thereof have valuable pharmacological properties, especially in the cardiovascular field. They act as calcium antagonists and have o-receptor-blocking properties and serotonin-antagonistic properties, as may be demonstrated, for example, in in vitro tests on isolated perfused mesenteric vessels of rats [Mc Gregor, D.: J. Physiol. 177, 21–30, (1965)] by way of the inhibition of potassium- and noradrenalininduced vasoconstriction, for example using 2,6-dimethyl-4-(3-nitrophenyl)-1,4-dihydropyridine-3,5-dicarboxylic acid 3-methyl ester 5-[2-[N-(4-(4-fluorophenyl)-4-oxo-n-butyl)-N-methylamino]ethyl ester] at a concentration of approx. $10^{-8}$ mol/liter ($IC_{50}$) for the inhibition of potassium-induced vasoconstriction, and at a concentration of approx. $3 \times 10^{-10}$ mol/liter ($IC_{50}$) for the inhibition of noradrenalin-induced vasoconstriction. It is also possible to demonstrate the bonding of the novel compounds or salts thereof to serotonin$_2$-receptors by means of the displacement of $^3$H-ketanserin from its bonding sites in membranes of rats' brains [Leysen J. E. et al.: Molecul. Pharmacol. 21, 301–304 (1982)], for example using 2,6-dimethyl-4-(3-nitrophenyl)-1,4-dihydropyridine-3,5-dicarboxylic acid 3-methyl ester 5-[2-[N-(4-(4-fluorophenyl)-4-oxo-n-butyl)-N-methylamino]ethyl ester] at a concentration of approx. $10^{-8}$mol/liter ($IC_{50}$).

The novel compounds or salts thereof have, in addition, an anti-hypertensive activity, as may be demonstrated, for example, by the reduction in blood pressure in renally hypertonic rats. For example, 2 hours after p.o. administration of 15 mg/kg of 2,6-dimethyl-4-(3-nitrophenyl)-1,4-dihydropyridine-3,5dicarboxylic acid 3-methyl ester 5-[2-[N-(4-(4-fluorophenyl)-4-oxo-n-butyl)-N-methylamino]ethyl ester] to renally hypertonic rats, a reduction in blood pressure of approx. 45 mm Hg may be observed.

The compouhds of the formula I and salts of such compounds may therefore be used, for example, as coronary dilators and antihypertensives for the treatment of cardio-vascular pathological conditions, such as *Angina pectoris* and its sequelae, vascular spasms, central and peripheral circulatory disorders, high blood pressure, arrhythmiae and cardiac insufficiency, and also for the inhibition of platelet aggregation or for the treatment of migraine. The novel compounds are, however, also valuable intermediates for the manufacture of other, especially pharmaceutically active, compounds.

The invention relates especially to novel compounds of the formula I in which R represents a mono- or bicyclic carbocyclic aryl radical or a five- or six-membered monocyclic heteroaryl radical containing as ring members from one to four ring nitrogen atoms, a ring oxygen or ring sulphur atom, or one or two ring nitrogen atoms together with a ring oxygen or a ring sulphur atom, which radical is bonded via a ring carbon atom to the carbon atom in the 4-position of the 1,4-dihydropyridine ring and optionally contains a fused benzo ring and is especially phenyl, naphthyl, pyrryl, pyrazolyl, imidazolyl, triazolyl, tetrazolyl, furyl, thienyl, isoxazolyl, oxazolyl, oxadiazolyl, isothiazolyl, thiazolyl, thiadiazolyl, pyridyl, pyridazinyl, pyrimidinyl, pyrazinyl, triazinyl, indolyl, isoindolyl, benzimidazolyl, benzoxadiazolyl, benzofuranyl, benzofurazanyl, benzothienyl, benzthiazolyl, 2,1,3-benzthiadiazolyl, quinolinyl or isoquinolinyl, wherein ring carbon atoms in these radicals may optionally be substituted by lower alkyl, lower alkenyl, lower alkynyl, lower alkylene, cycloalkyl, phenyl and/or phenyl-lower alkyl, it being possible for lower alkyl, phenyl or phenyl-lower alkyl optionally to contain as substituent(s) hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkyl-carbamoyl and/or cyano, and for cyclic radicals also to contain as substituent lower alkyl, which may in turn be substituted as indicated, and/or by hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, nitro, amino, N-lower alkylamino, N,N-di-lower alkylamino, N-lower alkyl-N-phenyl-lower alkylamino, lower alkyleneamino, oxa-lower alkyleneamino, thia-lower alkyleneamino and/or by aza-lower alkyleneamino in which the aza nitrogen atom may be substituted by lower alkyl, phenyl or phenyl-lower alkyl, it being possible for these radicals to contain as substituent(s) hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, carboxy, lower alkoxycarbonyl, carbamoyl, N-lower alkyl-carbamoyl, N,N-di-lower alkyl-carbamoyl and/or cyano, and for the cyclic radicals also to contain lower alkyl as substituent, and/or by lower alkanoylamino, azido, lower alkanoyl, carboxy, lower alkoxycarbonyl, carbamoyl, N-lower alkyl-carbamoyl, N,N-di-lower alkylcarbamoyl, cyano, sulpho, aminosulphonyl, N-lower alkylaminosulphonyl, N,N-di-lower alkylaminosulphonyl, lower alkylthio, lower alkylsulphinyl and/or by lower alkylsulphonyl, and/or wherein ring nitrogen atoms in these radicals R may optionally be substituted by lower alkyl that may optionally contain as substituent(s) hydroxy, lower alkoxy, lower alkoxy-lower alkoxy, halo-lower alkoxy, lower alkenyloxy, halo-lower alkenyloxy, lower alkynyloxy, lower alkylenedioxy, lower alkanoyloxy, halogen, carboxy, lower alkoxycarbonyl, carbamoyl, N-lower alkylcarbamoyl, N,N-di-lower alkylcarbamoyl or cyano, or by hydroxy or oxido, $R_1$ is lower alkyl, one of the radicals $R_2$ and $R_3$ represents lower alkyl and the other represents lower alkyl, cyano or amino, X represents oxygen or the group —NH—, $Alk_1$ represents lower alkylene, or phenyl-lower alkylene optionally substituted, especially in the phenyl moiety, by optionally etherified or esterified hydroxy, by lower alkyl or lower alkoxy each substituted by optionally etherified or esterified hydroxy, or by carboxy, lower alkoxycarbonyl or cyano, which lower alylene or phenyl-lower alkylene radical separates the group X from the nitrogen atom by from 2 to 8 carbon atoms, $R_4$ represents hydrogen, lower alkyl, or phenyl-lower alkyl optionally substituted, especially in the phenyl moiety, by optionally etherified or esterified hydroxy, by lower alkyl or lower alkoxy each substituted by optionally etherified or esterified hydroxy, Z represents the group —(C=O)— or a single bond, $Alk_2$ represents lower alkylene that separates the groups Z and Y by from 2 to 6 carbon atoms, Y represents the group —(C=O)— and $Ar_1$ represents a monocyclic carbocyclic aryl or heteroaryl radical, and is especially phenyl, naphthyl, pyrryl, furyl, thienyl or pyridyl, it being possible for these radicals to be substituted as defined above in connection with R, and to salts, especially pharmaceutically acceptable non-toxic acid addition salts of such compounds having salt-forming basic properties.

The invention relates especially to novel compounds of the formula I in which R and $Ar_1$ each represents phenyl or naphthyl that is optionally substituted by lower alkyl, phenyl and/or phenyl-lower alkyl, it being possible for such radicals, in turn, to contain as substituent(s) hydroxy, lower alkoxy, halo-lower alkoxy, lower alkylenedioxy, halogen, carboxy, lower alkoxycarbonyl and/or cyano and for the cyclic radicals also to contain as substituent lower alkyl, and/or by hydroxy, lower alkoxy, halolower alkoxy, lower alkenyloxy, halo-lower alkenyloxy, lower alkylenedioxy, halogen, nitro, amino, N-lower alkylamino, N,N-di-lower alkylamino, lower alkanoylamino, carboxy, lower alkoxycarbonyl, carbamoyl, cyano, sulpho, aminosulphonyl, N-lower alkylaminosulphonyl, N,N-di-lower alkylaminosulphonyl, lower alkylthio, lower alkylsulphinyl and/or by lower alkylsulphonyl, or R and $Ar_1$ each represents pyrryl, furyl, thienyl, pyridyl, 1-oxido-pyridyl or imidazolyl each bonded via a ring carbon atom and R may also represent benzofurazanyl or benzoxadiazolyl, wherein such radicals are optionally substituted in the manner indicated for a phenyl or naphthyl radical R or $Ar_1$, and may contain as substituent(s) especially lower alkyl, lower alkoxy, halogen and/or phenyl optionally substituted by lower alkyl, lower alkoxy, halogen and/or nitro, $R_1$ is lower alkyl, $R_2$ and $R_3$ each represents lower alkyl, or one of the groups $R_2$ and $R_3$ is lower alkyl and the other represents lower alkyl or cyano, X represents oxygen or the group —NH—, $Alk_1$ represents the group —$(CH_2)_n$— in which n represents an integer of from 2 to 6, $R_4$ represents hydrogen, lower alkyl or phenyl-lower alkyl, Z represents the group —(C=O)— or a single bond, $Alk_2$ represents the group —$(CH_2)_m$— in which m represents an integer of from 2 to 6, preferably from 2 to 4, and Y represents the group —(C=O)—, and to salts, especially pharmaceutically acceptable non-toxic acid addition salts of such compounds having salt-forming basic properties. The invention relates in addition to compounds of the formula I as defined immediately above in which $Alk_1$ represents the group —$(CH_2)n$— wherein n represents an integer of from 2 to 6 and wherein a hydrogen atom has been replaced by phenyl that is optionally substituted by lower alkyl, hydroxy, lower alkoxy, halo-lower alkoxy, lower alkylenedioxy, halogen, carboxy, lower alkoxycarbonyl and/or cyano.

The invention relates more especially to novel compounds of the formula I in which R and $Ar_1$ each represents phenyl that is optionally substituted by lower alkyl, hydroxy, lower alkoxy, halo-lower alkoxy, halolower alkenyloxy, lower alkylenedioxy, halogen, trifluoromethyl, nitro, lower alkanoylamino, phenyl or phenyl-lower alkyl each optionally substituted by optionally esterified or etherified hydroxy, and/or by cyano, it being possible for a phenyl radical R and $Ar_1$ to have one or more of the mentioned substituents which may be the same or different, or R and $Ar_1$ each represents pyridyl, furyl, 1-oxido-pyridyl or thienyl and R may also represent benzofurazanyl that may be substituted by lower alkyl or halogen, $R_1$, $R_2$ and $R_3$ each represents lower alkyl, X represents oxygen or the group —NH—, $Alk_1$ and $Alk_2$ each represents the group —$(CH_2)_n$— in which n represents an integer of from 2 to 4, $R_4$ represents hydrogen or lower alkyl, Z represents the group —(C=O)— or a single bond, and Y represents the group —(C=O)—, and to salts, especially pharmaceutically acceptable non-toxic acid addition salts of such compounds having salt-forming basic properties The invention relates in addition to compounds of the formula I as defined immediately above in which $Alk_1$ represents the group —$(CH_2)_n$ wherein n represents an integer of from 2 to 4 and wherein a hydrogen atom has been replaced by phenyl that is optionally substituted by lower alkyl, hydroxy, lower alkoxy, halo-lower alkoxy, lower alkylenedioxy, halogen, carboxy, lower alkoxycarbonyl and/or cyano.

The invention relates especially to novel compounds of the formula I in which R represents unsubstituted phenyl or preferably phenyl that is mono- or di-substituted by lower alkyl, by lower alkoxy, by halo-lower alkoxy or halo-lower alkenyloxy in which halogen has an atomic number of up to and including 35, by halogen having an atomic number of up to and including 35, by trifluoromethyl, by nitro and/or by cyano, the substituents occupying the 2- and/or 3-position(s), $R_1$, $R_2$ and $R_3$ each represents lower alkyl, X represents oxygen or the group —NH—, $Alk_1$ and $Alk_2$ each represents the group —$(CH_2)_n$— wherein n represents an integer of from 2 to 4, $R_4$ represents hydrogen or lower alkyl, Z represents a single bond, Y represents the group —(C=O)—, and $Ar_1$ represents phenyl or pyridyl, for example 2-pyridyl, 3-pyridyl or 4-pyridyl, each optionally substituted by halogen having an atomic number of up to and including 35, and to salts, especially pharmaceutically acceptable non-toxic acid addition salts of such compounds. The invention relates in addition to compounds of the formula I as defined immediately above in which $Alk_1$ represents the group —$(CH_2)_n$— wherein n represents an integer of from 2 to 4 and wherein a hydrogen atom has been replaced by phenyl that is optionally substituted by lower alkyl, lower alkoxy, hydroxy or halogen.

The invention relates especially to novel compounds of the formula I in which R represents phenyl that is mono- or di-substituted by halogen having an atomic number of up to and including 35, for example fluorine, chlorine or bromine, or mono-substituted by trifluoromethyl, nitro or cyano, the substituents occupying the 2- and/or 3-position(s), $R_1$, $R_2$ and $R_3$ each represents lower alkyl, especially methyl, X represents oxygen or the group —NH—, $Alk_1$ and $Alk_2$ each represents the group —$(CH_2)_n$— wherein n represents an integer of 2 or 3, $R_4$ represents hydrogen or lower alkyl, especially methyl, Z is a single bond, Y represents the group —(C=O)— and $Ar_1$ is phenyl optionally substituted by halogen having an atomic number of up to and including 35, for example fluorine, and to salts, especially pharmaceutically acceptable non-toxic addition salts of such compounds. The invention relates in addition to compounds of the formula I as defined immediately above, in which $Alk_1$ represents the group —$(CH_2)_n$— wherein n represents an integer of 2 or 3 and wherein a hydrogen atom has been replaced by phenyl.

The invention relates especially to novel compounds of the formula I in which R represents phenyl that is mono- or di-substituted by halogen having an atomic number of up to and including 35, for example fluorine, chlorine or bromine, or mono-substituted by nitro or cyano, the substituents occupying the 2- and/or 3-position(s), $R_1$, $R_2$ and $R_3$ each represents lower alkyl, especially methyl, X represents oxygen, $Alk_1$ and $Alk_2$ each represents the group —$(CH_2)_n$— wherein n represents an integer of 2 or 3, $R_4$ represents lower alkyl, especially methyl, Z is a single bond, Y represents the group —(C=O)— and $Ar_1$ represents phenyl substituted by halogen having an atomic number of up to and including 35, for example fluorine, and to salts, especially pharmaceutically acceptable non-toxic acid addition salts of such compounds.

The invention relates especially to compounds of the formula I in which R represents phenyl that is mono- or di-substituted in the 2- and/or 3-position(s) by halogen having an atomic number of up to and including 35 or mono-substituted in the 2- and/or 3-position(s) by nitro or cyano, $R_1$, $R_2$ and $R_3$ each represents lower alkyl having up to 4 carbon atoms, X represents oxygen, $Alk_1$ represents α,ω-alkylene having 2 or 3 carbon atoms that is unsubstituted or is substituted by phenyl, $Alk_2$ represents α,ω-alkylene having 2 or 3 carbon atoms, $R_4$ represents lower alkyl having up to 4 carbon atoms that is unsubstituted or is substituted by phenyl, Z is a single bond, Y represents the group —(C=O)— and $Ar_1$ represents phenyl or thienyl each of which is unsubstituted or substituted by halogen having an atomic number of up to and including 35, and to salts, especially pharmaceutically acceptable non-toxic acid addition salts of such compounds.

The invention relates especially to compounds of the formula I in which R represents phenyl that is mono- or di-substituted in the 2- and/or 3-position(s) by halogen having an atomic number of up to and including 35 or mono-substituted in the 2- and/or 3-position(s) by nitro or cyano, $R_1$, $R_2$ and $R_3$ each represents lower alkyl having up to 4 carbon atoms, X represents oxygen, $Alk_1$ and $Alk_2$ each represents unsubstituted α,ω-alkylene having 2 or 3 carbon atoms, $R_4$ represents lower alkyl having up to 4 carbon atoms, Z is a single bond, Y represents the group —(C=O)— and $Ar_1$ represents phenyl mono-substituted by halogen having an atomic number of up to and including 35, and to salts, especially pharmaceutically acceptable non-toxic acid addition salts of such compounds.

The invention relates especially to the compounds specifically described in the Examples.

The compounds of the formula I and salts of such compounds having salt-forming properties can be manufactured in a manner known per se, for example as follows:

(a) a compound of the formula

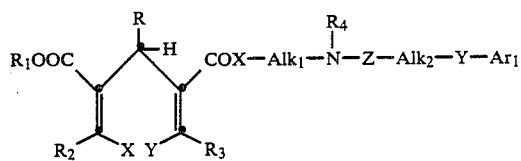

in which one of the radicals X and Y represents a group of the formula —NH$_2$ and the other represents hydroxy or a group of the formula —NH$_2$, or a tautomer thereof or a corresponding tautomeric mixture, is cyclised, or (b) a compound of the formula R-CHO (III) or a reactive functional derivative thereof is reacted with a compound of the formula

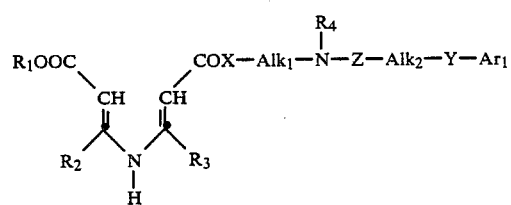

or with a tautomer thereof or a corresponding tautomeric mixture, or (c) in a compound of the formula

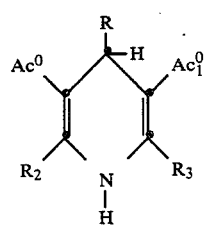

in which one of the radicals Ac$^o$ and Ac$_1^o$ represents a group that can be converted into the group —COOR$_1$ or into a radical of the formula

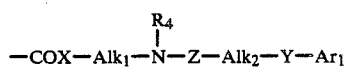

respectively, and the other represents the group —COOR$_1$ or a group of the formula Va or a radical that can be converted into the group —COOR$_1$ or into a group of the formula Va, respectively, the radical Ac$^o$ is converted into the group —COOR$_1$ and/or the radical Ac$_1^o$ is converted into a radical of the formula Va, or (d) a compound of the formula

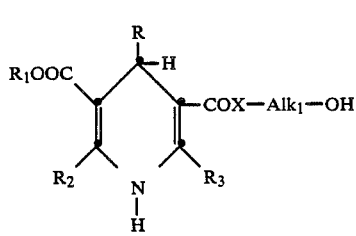

or a reactive ester thereof, is reacted with a compound of the formula

or (e) a compound of the formula

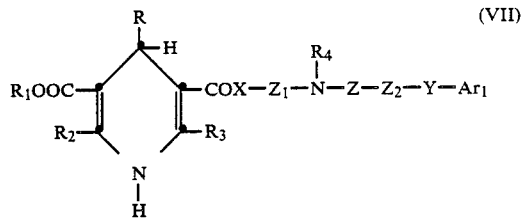

in which at least one of the groups Z$_1$ and Z$_2$ represents a group that can be converted by means of reduction into the group Alk$_1$ or Alk$_2$, respectively, and the other represents the group Alk$_1$ or Alk$_2$, respectively, or a group that can be converted by means of reduction into the group Alk$_1$ or Alk$_2$, respectively, the group Z$_1$ and/or the group Z$_2$ is(are) converted by means of reduction into the group Alk$_1$ or Alk$_2$, respectively, or, (f) a compound of the formula

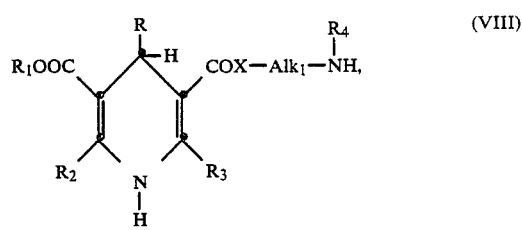

or a salt thereof, is reacted with a compound of the formula

or with a reactive derivative thereof, or (g) in a compound of the formula

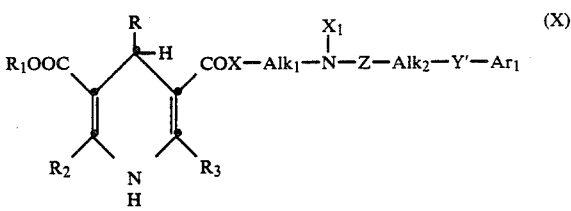

in which X$_1$ has the meaning of R$_4$ or represents a group that can be removed and replaced by hydrogen, Y' has the meaning of Y or represents a group that can be converted into the group Y, wherein at least one group X$_1$ that can be removed and replaced by hydrogen is removed and replaced by hydrogen and/or a group Y' having a different meaning from Y is converted into the group Y, a group X$_1$ having a different meaning from R$_4$ is removed and replaced by hydrogen and/or a group Y' having a different meaning from Y is converted into the group Y, if desired other protecting groups that are bonded to functional groups are removed and replaced by hydrogen, it being possible for the starting materials of the formulae II to X, if they have salt-forming properties, also to be used in the form of their salts, and the groups R, $R_1$, $R_2$, $R_3$, $R_4$, X, Z, $Alk_1$, $Alk_2$, Y and $Ar_1$ have the meanings given under formula I and, if desired, a resulting compound of the formula I is converted into a different compound of the formula I and/or, if desired, a resulting salt is converted into the free compound or into a different salt and/or, if desired, a resulting free compound of the formula I having salt-forming basic properties is converted into a salt and/or, if desired, a resulting mixture of racemates is separated into the pure racemates or diastereoisomers and/or a resulting racemate is separated into the optical antipodes.

Customarily, the starting materials of the formula II used in process variant (a) are formed in situ and the cyclisation according to the process can take place under the reaction conditions for the manufacture of the starting material. For example, the starting materials of the formula II and, under the reaction conditions, customarily also the corresponding end products of the formula I, can be obtained as follows:

(aa) a compound of the formula III or a reactive functional derivative thereof is reacted with a compound of the formula

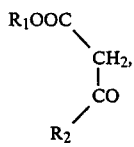

(XI)

a compound of the formula

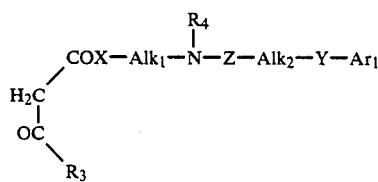

(XII)

and ammonia, or (ab) a compound of the formula III or a reactive functional derivative thereof is reacted with a compound of the formula

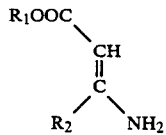

(XIII)

and a compound of the formula XII, or (ac) a compound of the formula III or a reactive functional derivative thereof is reacted with a compound of the formula

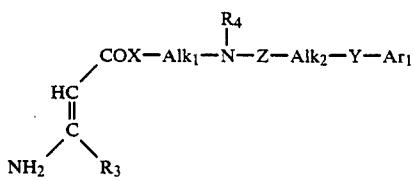

(XIV)

and a compound of the formula XI or XIII, or (ad) ammonia is reacted with a compound of the formula

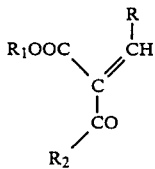

(XV)

and a compound of the formula XII, or (ae) ammonia is reacted with a compound of the formula

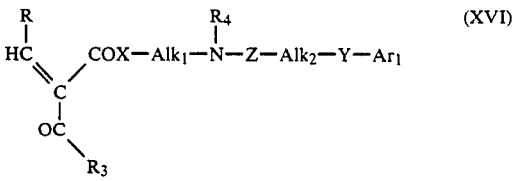

(XVI)

and a compound of the formula XI or XIII, or (af) ammonia is reacted with a compound of the formula

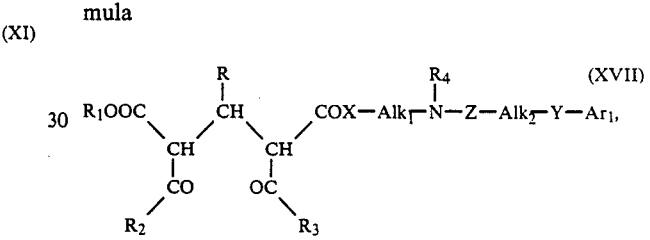

(XVII)

or (ag) a compound of the formula XIII is reacted with a compound of the formula XVI or of the formula

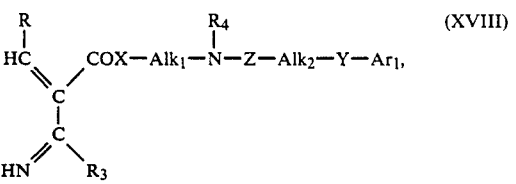

(XVIII)

or (ah) a compound of the formula XIV is reacted with a compound of the formula XV or with a compound of the formula

(XIX)

In these reactions the compounds of the formulae XI to XIX may also be used in the form of their tautomers or in the form of tautomeric mixtures; starting materials of the above formulae having salt-forming properties can also be used in the form of salts. In addition, the groups R, $R_1$, $R_2$, $R_3$, $R_4$, X, Z, $Alk_1$, $Alk_2$, Y and $Ar_1$ in the above-mentioned compounds have the meanings given in connection with formula I.

Reactive functional derivatives of the aldehyde of the formula III are, inter alia, the corresponding acetals, that is, the corresponding R-di-(etherified hydroxy)-methyl compounds, such as di-lower alkyl, for example dimethyl or diethyl, acetals or acylals, for example the corresponding diacyloxymethyl compounds, such as di-lower alkanoyl acylals, for example diacetyl acylals, or the corresponding dihalo, for example dichloro or dibromo, compounds, and also addition compounds, such as those with an alkali metal hydrogen sulphite, for example potassium hydrogen sulphite.

The ammonia used for the cyclisation reactions described above can also be used in the form of an agent that yields this compound in situ, for example in the form of an ammonium salt, such as ammonium acetate or ammonium hydrogen carbonate.

The cyclisation reaction (a), and the condensation reactions (aa) to (ah) for the manufacture of the starting material for the cyclisation reaction which is customarily formed in situ, are variants of the dihydropyridine synthesis according to Hantzsch. In variant (aa) a total of three molecules of water are removed; in further variants there occurs to some extent an addition reaction to the site of the water removal, that is to say, the water removal has already taken place during the manufacture of one or of two starting materials. In the reaction of compounds of the formula III with compounds of the formulae XIV and XIII according to step (ac), of compounds of the formula XIII with compounds of the formula XVIII according to step (ag) or of compounds of the formula XIV with compounds of the formula XIX according to step (ah), ammonia is removed in addition to or instead of water. If, in accordance with variant (aa), compounds of the formula I are to be manufactured in which $R_2$ and $R_3$ are different from one another, by-products may be formed that contain the same substituents in the 2- and 6-positions. By not placing the reactants together at the same time formation of such by-products can be reduced by promoting a particular course of reaction that proceeds in situ according to another variant since, corresponding to the staged addition of the reactants, for example first a compound of the general formula XIII or of the formula XIV may be produced.

The cyclisation and condensation reactions according to the process are carried out in a manner known per se, if necessary in the presence of a condensing agent, especially a basic condensing agent, such as an excess of a basic reactant or of an additional, for example organic, base, such as piperidine or ethyl diisopropylamine, or a metal alcoholate, such as an alkali metal lower alkoxide, and/or a suitable dehydrating or water-absorbing agent, and also customarily in the presence of an inert organic solvent, and at reaction temperatures in the range of from approximately room temperature to approximately 150° C., especially at the boiling temperature of the solvent. If desired, the reaction is carried out in an inert gas atmosphere, for example a nitrogen atmosphere, and/or, for example when using a low-boiling solvent and/or ammonia, in a closed vessel under elevated pressure.

The starting materials used in the process variants are known or can be manufactured according to processes that are known per se.

For example, starting materials of the formula XII can be produced by reacting compounds of the formula

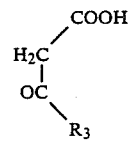
(XIIa)

with compounds of the formula

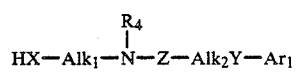
(XIIb)

in customary manner. Instead of carboxylic acids of the formula XIIa it is also possible to use functional derivatives thereof, such as corresponding carboxylic acid anhydrides, especially mixed anhydrides, such as those with lower alkanecarboxylic acids, for example formic acid, also acid halides, for example corresponding chlorides and bromides, also acid azides, and furthermore activated esters, for example cyanomethyl ester. These can be reacted to form compounds of the formula XII, optionally in the presence of condensing agents, by reaction with a compound of the formula XIIb, and free carboxylic acids of the formula XIIa can be reacted to form compounds of the formula XII also by reaction with compounds of the formula XIIb in which the azido group stands in place of the group HX—. Carboxylic acids of the formula XIIa can also be reacted in the form of salts, especially alkali metal or alkaline earth metal salts, with reactive esters of alcohols of the formula XIIb in which X represents oxygen, such as corresponding halides, for example chlorides, bromides or iodides, or organic sulphonic acid esters, for example lower alkanesulphonic or arenesulphonic acid esters, such as methanesulphonic or p-toluenesulphonic acid esters, to form corresponding carboxylic acid esters, or corresponding hydrolysable imino esters, such as corresponding imino-lower alkyl esters, are hydrolysed to the esters. Imino esters of this kind can be obtained in customary manner, for example from nitriles of the formula

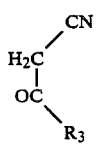
(XIIc)

that correspond to compounds of the formula XIIa, by reaction with compounds of the formula XIIb in which X represents oxygen, in the presence of an acidic condensing agent, for example hydrogen chloride, in a suitable solvent, for example one of inert character, such as an aromatic compound, for example benzene.

Compounds of the formula XIIb can, in turn, be obtained in a manner known per se by the reaction of compounds of the formula

(XIId)

in which the hydroxy group may be present in reactive esterified form, such as, for example, in the form of a halogen, for example chlorine, bromine or iodine, or a sulphonyloxy group, for example an arylsulphonyloxy group, such as p-toluenesulphonyloxy, with compounds of the formula

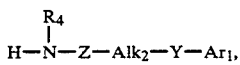

(XIIe)

advantageously in the presence of a condensing agent, for example one of basic character, such as an oxide, hydroxide or carbonate of an alkali metal or alkaline earth metal, such as sodium hydroxide or calcium carbonate, and customarily in the presence of a solvent, for example a lower alkanol, such as ethanol, at elevated or reduced temperature. Compounds of the formula XIIe can also be used in the form of their metal derivatives in which the hydrogen atom positioned at the nitrogen has been replaced by a suitable metal, such as lithium or potassium. In such cases, the described reaction with compounds of the formula XIId is carried out in an inert anhydrous solvent, for example one of ethereal character, such as tetrahydrofuran, or an aromatic solvent, for example toluene, advantageously under a protective gas, such as nitrogen.

Metal compounds corresponding to the formula XIIe can be obtained in customary manner, for example by reaction with a suitable alkali metal organic compound, for example butyllithium, in an anhydrous solvent, such as tetrahydrofuran, advantageously under a protective gas, for example argon, it being possible to use the metal compound contained in the reaction mixture for the above-described reaction without its having been isolated.

Compounds of the formula XIIe can in turn be manufactured in a manner known per se, for example by the reaction of a compound of the formula

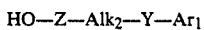 (XIIf)

or a reactive derivative thereof, with an amine of the formula

 (XIIg).

If Z in the formula XIIf is a group $-(C=O)-$, the carboxylic acid of the formula XIIf forming its basis can also be ssed in the form of a functinal derivative, for example in the form of a corresponding carboxylic acid anhydride, especially a mixed anhydride, such as one with lower alkanecarboxylic acids, for example formic acid, also in the form of an acid halide, for example a corresponding chloride or bromide, in the form of an acid azide, and furthermore in the form of an activated ester, for example cyanomethyl ester. These may be reacted in customary manner, optionally in the presence of condensing agents, for example those of basic character, for example tertiary amines, such as N-ethyl-N,N-diisopropylamine, or an excess of the amine of the formula XIIg to be reacted, with an amine of the formula XIIg to form a compound of the formula XIIe in which Z is the group $-(C=O)-$.

If Z in the formula XIIf is a single bond, the corresponding alcohol may also be in the form of a reactive ester, for example a halide, such as a chloride or bromide, or in the form of a sulphonic acid ester, such as a methanesulphonic or p-toluenesulphonic acid ester, which is used with an amine of the formula XIIg, customarily in the presence of a condensing agent, for example one of basic character, such as a carbonate, oxide or hydroxide of an alkali metal or alkaline earth metal, for example sodium carbonate or hydroxide. Such reactions are advantageously carried out in an inert solvent, for example one of aromatic character, such as benzene or toluene, for the reaction of reactive carboxylic acid derivatives with an amine of the formula XIIg, or a lower alkanol, such as ethanol, for the reaction of reactive esterified alkanols of the formula XIIf with an amine of the formula XIIg. The latter can also be used in the form of an N-metal derivative, for example an alkali metal derivative, such as one with lithium, such reactions usually being carried out in an ethereal solvent, such as di-n-butyl ether, and under a protective gas, such as nitrogen or argon.

The reaction of free carboxylic acids of the formula XIIa with compounds of the formula XIIb is advantageously carried out in the presence of an acidic catalyst that promotes water removal, such as a protonic acid, for example hydrochloric, hydrobromic, sulphuric, phosphoric or boric acid, benzenesulphonic or toluenesulphonic acid, or a Lewis acid, for example boron trifluoride etherate, in an excess of the alcohol used and/or in an inert solvent, if necessary with the distillative, for example azeotropic, removal of the water freed during the reaction. Furthermore, the reactions can also be carried out in the presence of water-binding condensing agents, such as suitably substituted carbodiimides, for example N,N'-diethyl-, N,N'-dicyclohexyl- or N-ethyl-N'-(3-dimethylaminopropyl)-carbodiimide, in inert organic solvents. Mixed anhydrides, especially acid halides, are reacted, for example, in the presence of acid-binding agents, for example organic, especially tertiary nitrogen bases, such as triethylamine, ethyldiisopropylamine or pyridine, or also inorganic bases, for example alkali metal or alkaline earth metal hydroxides or carbonates, such as sodium, potassium or calcium hydroxide or carbonate, with alcohols or with alcoholates, for example alkali metal lower alkoxides.

The reactions of reactive esters, for example cyanomethyl or pentachlorophenyl esters, with compounds of the formula XIIb are carried out, for example, in a solvent that is inert towards the reactants, in a temperature range of from approximately 0° C. to approximately 120° C., preferably at from room temperature up to approximately 60° C.

The hydrolysis of imido ester starting materials is carried out, for example, by means of aqueous mineral acids, such as hydrochloric acid or sulphuric acid, it being possible to hydrolyse the imino ester salts, for example hydrochlorides, obtained by the addition of hydrogen chloride to nitriles and reaction with anhydrous alcohols, especially unsubstituted or substituted lower alkanols, directly to the corresponding esters after the addition of water. It is also possible to obtain the desired ester compound of the formula XI, for example, from a mixture of nitrile, alcohol and sulphuric acid with a suitable water content without isolation of the imido ester formed in situ.

Starting materials of the formulae XIV, XVI, XVII and XVIII can be manufactured from corresponding starting materials in an analogous and customary manner.

Starting materials of the formula IV are formed in situ, analogously to the manufacture of starting materials of the formula II, and the cyclisation according to the process to form the end products of the formula I can be carried out in the same reaction mixture under the conditions given for the manufacture of the starting materials. Accordingly, starting materials of the formula IV can be obtained by reacting compounds of the formula XII with those of the formula XI and ammonia, or compounds of the formula XII with those of the formula XIII, or compounds of the formula XIV with those of the formula XI or XIII, such reactions customarily being carried out in a suitable solvent, for example a lower alkanol, such as ethanol, optionally at elevated or reduced temperature, advantageously under a protective gas, such as nitrogen.

Starting materials of the formula V may be, according to the radical or radicals $Ac^o$ contained in them, for example, carboxylic acids ($Ac^o$ is carboxy), carboxylic acid anhydrides, especially mixed anhydrides, such as acid halides, for example chlorides or bromides, or azides ($Ac^o$ is halo-carbonyl, for example chloro- or bromo-carbonyl, or azidocarbonyl), also activated esters, for example cyanomethyl ester ($Ac^o$ is cyanomethoxycarbonyl); these may be converted into the corresponding esters by treatment with a corresponding alcohol, optionally in the presence of condensing agents, for example for the conversion of the group $Ac^o$ into an ester group corresponding to the group $-COOR_1$, by reaction with a lower alkanol corresponding to the meaning of $R_1$, or with a reactive derivative thereof, for example a corresponding alcoholate, and free carboxylic acids also by reaction with suitable diazo compounds, such as diazo-lower alkanes, compounds of the formula I being formed that contain the group $-COOR_1$.

For the conversion of the group $Ac_1^o$ into the group of the above-defined formula Va, a starting material of the formula V in which $Ac_1^o$ is carboxy, the radical of an anhydride, especially a mixed anhydride, such as an acid halide, for example chloride or bromide, or an azide, or an activated ester, such as a cyanomethyl ester, is reacted with a compound of the formula XIIb in customary manner. Carboxylic acid esters of the type indicated in which X represents oxygen can also be obtained by using as starting materials salts, especially alkali metal or alkaline earth metal salts, of the free carboxylic acids, and treating these with reactive esters of alcohols corresponding to the compounds of the formula XIIb in which X is oxygen, such as corresponding halides, for example chlorides, bromides or iodides, or organic sulphonic acid esters, for example lower alkanesulphonic or arenesulphonic acid esters, such as methanesulphonic or p-toluenesulphonic acid esters, or by hydrolysing corresponding hydrolysable imino esters, such as corresponding imino-lower alkyl esters, to the esters.

Imino esters of this kind can be obtained, for example, from starting materials of the formula V in which $Ac^o$ represents the cyano group, by reaction with a lower alkanol corresponding to the meaning of $R_1$ and/or with an alcohol of the formula XIIb in which X is oxygen, in the presence of an acidic condensing agent, such as hydrogen chloride or concentrated sulphuric acid.

The reaction of free carboxylic acids with alcohols, such as lower alkanols, or with compounds of the formula XIIb, is advantageously carried out in the same manner as described hereinbefore for the reaction of carboxylic acids of the formula XIIa with compounds of the formula XIIb.

The reactions of reactive esters corresponding to the formula V, for example cyanomethyl, benztriazol-1-yl or pentachlorophenyl esters, with lower alkanols corresponding to the meaning of $R_1$ or with compounds of the formula XIIb are carried out, for example, in a solvent inert towards the reactants in a temperature range of from approximately 0° C. to approximately 120°, preferably at from room temperature up to approximately 60° C.

Also the hydrolysis of imido ester starting materials is carried out, for example, as described hereinbefore in connection with process variant (a).

Starting materials of the formula V having a free carboxy group $Ac^o$ can be obtained, for example, by manufacturing the corresponding 2-cyanoethyl ester, there being used, for example in one of the aforedescribed processes (af) or (ag), a compound of the formula XIII in which there is a 2-cyanoethoxycarbonyl group in place of the group $-COOR_1$; for example, a 3-aminocrotonic acid 2-cyanoethyl ester containing the group $R_2$ can be reacted with the other reactants and then the resulting 2-cyanoethyl ester compound can be cleaved under mild conditions, for example by means of aqueous or aqueous alkanolic 1N sodium hydroxide at room temperature, to form the free carboxylic acid. The latter can, if necessary, be converted in a manner known per se into the desired reactive functional derivative.

The nitrile compounds of the formula V that also come into consideration as starting materials for process variant (c) can be manufactured, for example, analogously to one of the process variants (aa) to (ah) by using starting materials that contain a cyano group in place of the radical $-COOR_1$, such as, for example, 3-aminocrotononitrile containing the group $R_2$ instead of a compound of the formula XIII.

The starting materials of the formula VI required for process variant (d) can be manufactured in a manner known per se, for example analogously to the reactions described in the process steps (aa) to (ah), there being used instead of the compounds XII, XIV, XVI, XVII or XVIII those starting materials that contain in place of a group of the formula

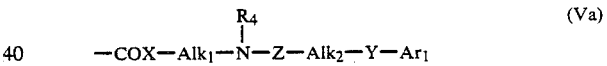

a group of the formula $-COX-Alk_1-OH$ (VIb) or a reactive ester thereof. Reactive esters are, for example, esters formed with a hydrohalic acid, for example hydrochloric acid, or an organic sulphonic acid, such as an arylsulphonic acid, for example p-toluenesulphonic acid, in which the hydroxy group, therefore, has been replaced, for example, by halogen, such as chlorine or bromine, or, for example, by arylsulphonyloxy, such as p-toluenesulphonyloxy. For example, a starting material of the formula

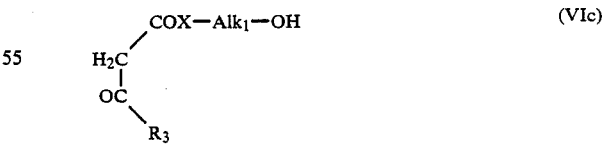

can be obtained analogously to the methods described for the manufacture of starting materials of the formula XII, for example by the reaction of compounds of the formula XIIa with compounds of the formula $HX-Alk_1-OH$ (XIId) or a reactive ester, for example a halide, such as bromide or iodide, thereof as described. Alternatively, a nitrile of the formula XIIc is reacted with a compound of the formula XIId in which X represents oxygen, in the presence of an acidic condensing agent, for example hydrogen chloride, to form the corresponding imino ester salt, which is then hydrolysed by means of water in an acidic medium, for example in the manner described above, to form the corresponding carboxylic acid ester.

The above reactions and also process variant (d) can be carried out under reaction conditions that are known per se, in the absence or customarily the presence of solvents or diluents, depending on the nature of the reaction and/or reactants at elevated or reduced temperature, for example in a temperature range of from approximately $-10°$ C. to approximately $150°$ C., under atmospheric pressure or in a closed vessel, optionally under pressure, and/or in an inert atmosphere, for example a nitrogen atmosphere.

The groups $Z_1$ and $Z_2$ required for process variant (e) that can be converted by means of reduction into the groups $Alk_1$ and $Alk_2$, respectively, contain C—C double and/or triple bonds and/or carbonyl or thiocarbonyl groups in the corresponding alkylene radical.

The reduction of unsaturated groups to the carbon-carbon single bond is carried out, for example, by means of activated hydrogen, such as hydrogen in the presence of a hydrogenation catalyst, for example a nickel, platinum or palladium catalyst, whilst the reduction of carbonyl groups to the methylene group may be carried out by means of hydrogen in the presence of, for example, a copper chromite catalyst, or according to Clemmensen's method, for example by means of zinc or a zinc amalgam in a mineral acid, for example hydrochloric acid. The reduction of thiocarbonyl groups can be effected in a similar manner, for example using a sulphur-resistant catalyst. The reduction of the above-mentioned groups can also be effected by means of a hydride reducing agent, for example sodium borohydride or diborane. In these reduction reactions care must be taken, if desired, that other groups that are sensitive to reduction, for example unsaturated groups or nitro groups, are not attacked, for example by selecting a suitable reducing agent, the amount thereof necessary for carrying out the reduction and/or suitable process conditions, for example elevated or reduced temperature, and/or by using a suitable solvent. These reactions are carried out in a manner known per se, customarily in the presence of solvents and diluents, depending on the nature of the reduction and/or the reactants at reduced or elevated temperature, for example in a temperature range of from approximately $-15°$ C. to approximately $120°$ C. under normal pressure or in a closed vessel, optionally under pressure and/or under a protective gas, for example nitrogen.

Starting materials of the formula VII can be manufactured according to methods known per se, for example analogously to the processes described under (a) to (d). For example, it is possible to proceed analogously to the reaction steps described in the steps, (aa) to (ah) using instead of compounds XII, XIV, XVI, XVII or XVIII those compounds that contain instead of the above-defined group Va a group of the formula

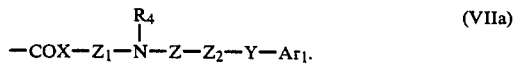

(VIIa)

For example, a starting material of the formula

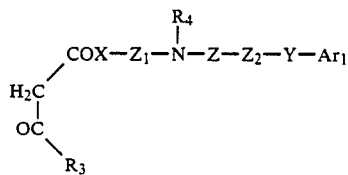

can be produced analogously to the methods described for the manufacture of compounds of the formula XII, for example starting from compounds of the formula XIIa or reactive derivatives thereof, for example anhydrides, acid halides, for example chlorides, azides, mixed esters such as cyanomethyl esters or pentachlorophenol esters. Carboxylic acids of the formula XIIa can also be reacted in the form of salts, especially alkali metal or alkaline earth metal salts, with reactive esters of the formula

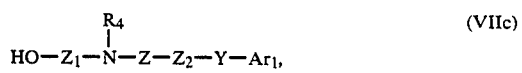

such as corresponding halides, for example chlorides, bromides or iodides, or organic sulphonic acid esters, such as those with lower alkanesulphonic acids, such as methanesulphonic acid, or arylsulphonic acids, such as benzenesulphonic acid, to form corresponding carboxylic acid esters. Alcohols of the formula VIIc can, on the other hand, be reacted with nitriles of the formula XIIc in customary manner in the presence of an acidic condensing agent, such as a mineral acid, for example hydrochloric or sulphuric acid, to form the salts of corresponding imino esters, which are then hydrolysed by means of water, in the manner described, to form the carboxylic acid esters. These reactions are carried out under customary reaction conditions that are known per se. Starting materials of the formula VIIc can in turn be obtained in customary manner, for example by reacting compounds of the formula $HO-Z_1-A$ (VIId) in which A is a suitable leaving group, for example a halogen, such as chlorine, bromine or iodine, or a sulphonyloxy group, such as p-toluenesulphonyloxy, with compounds of the formula XIIe.

If the group Z in the starting materials of the formula IX required for process variant (f) represents the group $-(C=O)-$, the coresponding carboxylic acid can also be used in the form of a functional derivative, for example a corresponding carboxylic acid anhydride, especially a mixed anhydride, such as one with lower alkanecarboxylic acids, for example formic acid, or in the form of an acid halide, for example a corresponding chloride or bromide, or an acid azide, or in the form of an activated ester, for example cyanomethyl ester.

The reaction of free carboxylic acids of the formula IX with compounds of the formula VIII is advantageously carried out in the same manner as described hereinbefore for the reaction of carboxylic acids of the formula XIIa with compounds of the formula XIIb.

The reactions of reactive esters, for example cyanomethyl or pentachlorophenyl esters of the formula IX, with compounds of the formula VIII are carried out, for example, in a solvent that is inert towards the reactants, in a temperature range of from approximately $0°$ C. to approximately $120°$ C., preferably at from room temperature to approximately $60°$ C.

If Z in the formula IX represents a single bond, the hydroxy group may also be present in reactive esterified form, such as, for example, in the form of a halogen, for example chlorine, bromine or iodine, or in the form of a sulphonyloxy group, for example an arylsulphonyloxy group, such as p-toluenesulphonyloxy, which is reacted with an amine of the formula VIII advantageously in the presence of a condensing agent, for example one of basic character, such as an oxide, hydroxide or carbonate of an alkali metal or alkaline earth metal, such as sodium hydroxide or calcium carbonate, and customarily in the presence of a solvent, for example a lower alkanol, such as ethanol, at elevated or reduced temperature. Compounds of the formula VIII can also be used in the form of their metal derivatives in which the hydrogen atom positioned at the nitrogen has been replaced by a suitable metal, such as lithium or potassium. In such cases the described reaction with compounds of the formula IX in which, for example, a halogen such as, for example chlorine, stands in place of the hydroxy group, is carried out in an inert anhydrous solvent, for example one of ethereal character, such as tetrahydrofuran, or an aromatic solvent, for example toluene, advantageously under a protective gas, such as nitrogen.

Metal compounds corresponding to the formula VIII can be obtained in customary manner, for example by reaction with a suitable alkali metal organic compound, for example butyllithium, in an anhydrous solvent, such as tetrahydrofuran, advantageously under a protective gas, for example argon, it being possible for the metal compound contained in the reaction mixture to be used for the above-described reaction without having to be isolated.

Starting materials of the formula VIII can be formed in situ analogously to the method described for the manufacture of starting materials of the formula II, it being possible for the cylisation to compounds of the formula VIII to be carried out under the specified conditions in the same reaction mixture. Accordingly, starting materials of the formula VIII can be obtained, for example, by reacting compounds of the formula XV or XIX with compounds of the formula

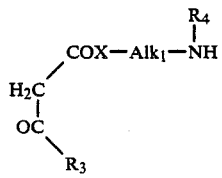
(XIIh)

or of the formula

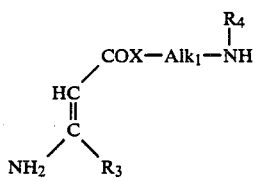
(XIVa)

with ammonia; or compounds of the formula XI or XIII may be reacted with those of the formula

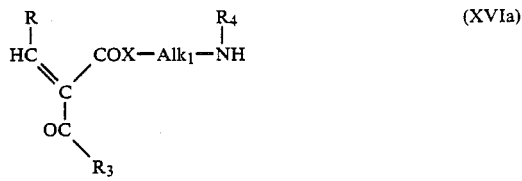
(XVIa)

or of the formula

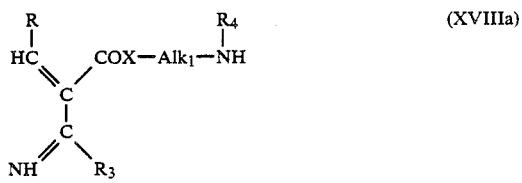
(XVIIIa)

or compounds of the formula

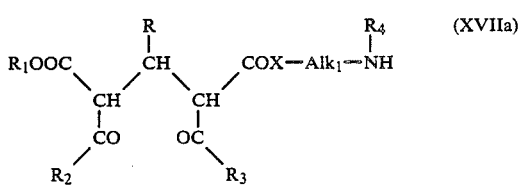
(XVIIa)

may be reacted as the case may be with ammonia to form starting materials of the formula VIII, such reactions customarily being carried out in a suitable solvent, for example a lower alkanol, such as ethanol, optionally at elevated or reduced temperature, advantageously under a protective gas, such as nitrogen. Instead of forming the 1,4-dihydropyridine ring in situ, it is, however, also possible to start from pre-formed carboxylic acids of the formula

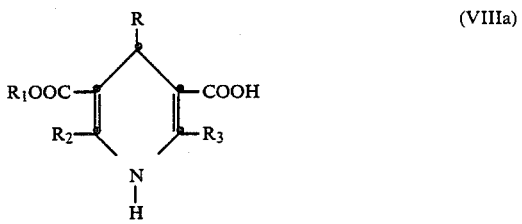
(VIIIa)

and to react these with compounds of the formula HX—Alk$_1$—NHR$_4$ (VIIIb). Instead of carboxylic acids of the formula (VIIIa) it is possible to use functional derivatives thereof, such as corresponding carboxylic acid anhydrides, especially mixed anhydrides, such as those with lower alkanecarboxylic acids, for example formic acid, also acid halides, for example corresponding chlorides or bromides, also acid azides, and also activated esters, for example cyanomethyl ester. These may be reacted to form compounds of the formula VIII, optionally in the presence of condensing agents, by reaction with a compound of the formula VIIIb, and free carboxylic acids of the formula VIIIa may also be reacted to form compounds of the formula VIII by reaction with compounds of the formula VIIIb in which the azido group stands in place of the group HX—. Carboxylic acids of the formula VIIIa can also be reacted to form corresponding carboxylic acid esters in the form of salts, especially alkali metal or alkaline earth metal salts with reactive esters of alcohols of the formula VIIIb in which X represents oxygen, such as corresponding halides, for example chlorides, bromides or iodides, or with esters of organic sulphonic acids, for example lower alkanesulphonic acid or arenesulphonic acid esters, such as methanesulphonic or p-toluenesulphonic acid esters; or corresponding hydrolysable imino esters, such as corresponding imino lower alkyl esters, are hydrolysed, for example by means of aqueous mineral acids, such as hydrochloric acid, to the esters. Imino esters of this kind can be obtained in customary manner, for example from nitriles of the formula

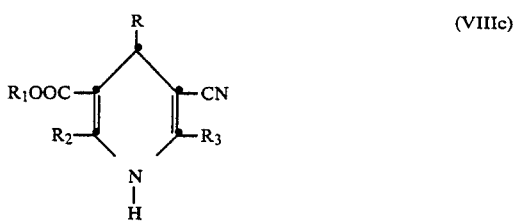

(VIIIc)

by reaction with compounds of the formula VIIIb in which X represents oxygen, in the presence of an acidic condensing agent, for example hydrogen chloride, in a suitable solvent, for example one of inert character, such as an aromatic substance, for example benzene.

Process variant (f) and also the reactions described hereinafter can be carried out under reaction conditions that are known per se, in the absence or, customarily, the presence of solvents or diluents, depending on the nature of the reaction and/or reactants at reduced or elevated temperature, for example in a temperature range of from approximately −10° C. to approximately 150° C., under atmospheric pressure or in a closed vessel, optionally under pressure and/or in an inert atmosphere, for example a nitrogen atmosphere.

Protected functional groups according to process variant (g) are, for example, protected hydroxy and/or amino groups contained in the aromatic radicals R and/or $Ar_1$, the protecting groups being groups that can be removed and replaced by hydrogen. A group Y′ that can be converted into the group Y is a functionally modified and thus protected derivative of the group —(C=O)—, from which the latter can be formed. Functional derivatives of the group —(C=O)— are, for example, acetals, such as di-lower alkyl acetals, for example dimethyl or diethyl acetals, and also cyclic acetals, such as, for example, ethylene acetal, specifically the corresponding dioxolan, and also addition compounds, such as those with bisulphites, for example an alkali metal hydrogen sulphide, for example potassium hydrogen sulphite.

The removal of the group $X_1$ and of hydroxy- and/or amino-protecting groups is effected by means of solvolysis, such as hydrolysis, alcoholysis or acidolysis, or by means of reduction, including hydrogenolysis, the group Y′ corresponding to a functionally modified derivative of the group —(C=O)— being converted into the group —(C=O)— by means of hydrolysis, especially by means of acid hydrolysis.

An especially suitable removable hydroxy- or amino-protecting group is especially an α-aryl-lower alkyl group that can be removed by hydrogenolysis, such as an optionally substituted 1-polyphenyl-lower alkyl group or a 1-phenyl-lower alkyl group, for example benzhydryl or trityl, in which substituents, especially of the phenyl moiety, may be, for example, lower alkyl, such as methyl, or lower alkoxy, such as methoxy, and especially benzyl, whilst a removable group $X_1$ and hydroxy- and/or amino-protecting groups are radicals that can be removed by solvolysis, such as hydrolysis or acidolysis, also by reduction, including hydrogenolysis, especially a corresponding acyl radical, such as the acyl radical of an organic carboxylic acid, for example lower alkanoyl, such as acetyl, or aroyl, such as benzoyl, and also the acyl radical of a semi-ester of carbonic acid, such as lower alkoxycarbonyl, for example methoxycarbonyl, ethoxycarbonyl, or tert.butoxycarbonyl, 2-halolower alkoxycarbonyl, for example 2,2,2-trichloroethoxycarbonyl or 2-iodoethoxycarbonyl, optionally substituted 1-phenyl-lower alkoxycarbonyl, for example benzyloxycarbonyl or diphenylmethoxycarbonyl, or aroylmethoxycarbonyl, for example phenacyloxycarbonyl, and also an optionally substituted 1-polyphenyl-lower alkyl group, for example as mentioned above, and especially trityl.

Hydrogenolytically removable radicals $X_1$, especially optionally substituted 1-phenyl-lower alkyl groups, and also suitable acyl groups, such as optionally substituted 1-phenyl-lower alkoxycarbonyl, and hydroxy- and/or amino-protecting groups of this kind present in the aromatic radicals R and/or $Ar_1$ can be removed by treatment with catalytically activated hydrogen, for example with hydrogen in the presence of a catalyst, such as a suitable noble metal catalyst, for example palladium or platinum, it being necessary to take care that a phenyl-lower alkyl, specifically benzyl, group corresponding to the group $X_1$ if desired is not removed, for example by means of volumetric control of the amount of hydrogen absorbed and timely discontinuation of the hydrogenation and/or by selection of a suitable catalyst and/or solvent.

Hydrolytically removable groups $X_1$, such as acyl radicals of organic carboxylic acids, for example lower alkanoyl, and of semiesters of carbonic acid, for example lower alkoxycarbonyl, and also, for example, trityl radicals, and protecting groups of this kind positioned at functional groups, such as at hydroxy and/or amino groups, in the radicals R and $Ar_1$, can be removed, depending on the nature of the groups, by treating with water under acidic or basic conditions, for example in the presence of a mineral acid, such as hydrochloric or sulphuric acid, and this applies especially also to acetals corresponding to the meaning of Y′, or in the presence of an alkali metal or alkaline earth metal hydroxide or carbonate or an amine, such as isopropylamine.

Acidolytically removable radicals $X_1$ and/or protecting groups positioned at functional groups, for example at hydroxy and/or amino, in a radical R and/or $Ar_1$ are specially certain acyl radicals of semi-esters of carbonic acid, such as, for example, tert.-lower alkoxycarbonyl radicals or optionally substituted diphenylmethoxycarbonyl radicals, and also a tert.-lower alkyl radical; such radicals can be removed, for example, by treatment with suitable strong organic carboxylic acids, such as lower alkanecarboxylic acids optionally substituted by halogen, especialy fluorine, especially with trifluoroacetic acid (if necessary in the presence of an activating agent, such as anisole), and with formic acid.

Reductively removable radicals $X_1$ and/or protecting groups positioned at functional groups in a radical R and/or $Ar_1$, for example the mentioned hydroxy and/or amino groups, also include those groups that are removed on treatment with a chemical reducing agent (especially with a reducing metal or a reducing metal compound). Such radicals are especially 2-halo-lower alkoxycarbonyl or arylmethoxycarbonyl, which can be removed, for example, by treatment with a reducing heavy metal, such as zinc, or with a reducing heavy metal salt, such as a chromium(II) salt, for example a chromium(II) chloride or acetate, customarily in the presence of an organic carboxylic acid, such as formic acid or acetic acid, and water.

Protecting groups that are positioned at functional hydroxy and/or amino groups present in a radical R and/or Ar$_1$ correspond to the aforementioned groups that can be removed by means of the described methods and replaced by hydrogen, such groups being removed in the course of the described process at the same time as other groups or subsequently in a separate process step.

The above reactons are customarily carried out in the presence of a solvent or solvent mixture, it also being possible for suitable reactants simultaneously to act as such, and, if necessary, while cooling or heating, for example in an open or closed vessel and/or in the atmosphere of an inert gas, for example nitrogen.

Starting materials of the formula X can be manufactured in manner known per se, for example analogously to the processes described under (a) to (f). For example, it is possible to proceed analogously to the reaction steps described in stages (aa) to (ah) using, in place of compounds of the formula XII, XIV, XVI, XVII or XVIII, compounds that contain instead of the above-defined group Va a group of the formula

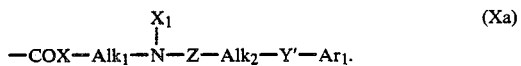
$$-COX-Alk_1-\overset{X_1}{\underset{|}{N}}-Z-Alk_2-Y'-Ar_1. \quad (Xa)$$

A starting material containing the group Xa and corresponding analogously to the formula XII can be obtained analogously to the process steps described for that.

Starting materials of the formula X can furthermore be obtained by reacting compounds of the abovedefined formula VI with substances of the formula

$$\overset{X_1}{\underset{|}{HN}}-Z-Alk_2-Y'-Ar_1 \quad (Xb)$$

that are structurally analogous to those of the formula XIIe, it being possible for the manufacture of starting materials of the formula Xb to be effected again analogously to the procedure described for the reaction of compounds XIIf with those of the formula XIIg.

These reactions are carried out in a manner known per se, customarily in the presence of solvents or diluents, at elevated or reduced temperature, for example in a temperature range of from approximately $-15°$ C. to approximately 150° C. under normal pressure or in a closed vessel optionally under pressure and/or under a protective gas, such as nitrogen.

Compounds of the formula I obtainable according to the process can be converted in a manner known per se into other compounds of the formua I, for example by converting substituents contained in compounds of the formula I into other substituents included within formula I.

For example, an esterified carboxy group $-COOR_1$ can be converted into a different ester group by transesterification. For this there are preferably used corresponding alcohol compounds that have a boiling point distinctly above that of the alcohol of the esterified group in the compound of the formula I to be converted, and the reaction is carried out, for example, in an excess of the hydroxy compound and/or an inert organic solvent that preferably also has a boiling point distinctly above that of the alcohol of the esterified group, preferably in the presence of a catalyst, for example an alkali metal lower alkoxide, such as sodium or potassium methoxide or ethoxide, with the application of heat and customarily with distillative removal of the alcohol freed.

Compounds of the formula I in which R$_4$ represents benzyl can be converted, by removal of the benzyl group and replacement thereof with hydrogen, into compounds of the formula I in which R$_4$ is hydrogen. Suitable for such a removal is catalytic debenzylation by means of hydrogen in the presence of a hydrogenation catalyst, for example platinum or Raney nickel. Conversely, compounds of the formula I in which R$_4$ is hydrogen can be converted into compounds of the formula I in which R$_4$ is a phenyl-lower alkyl group, for example by reaction with a phenyl-lower alkanol of which the hydroxy group may be in reactive esterified form, for example in the form of a halide, such as a chloride or bromide. More advantageously, such reactions are carried out in the presence of basic agents, for example an oxide or hydroxide or carbonate of an alkali metal or alkaline earth metal, such as sodium hydroxide, calcium hydroxide or calcium carbonate, and customarily in the presence of a solvent, such as a lower alkanol, for example ethanol.

Compounds of the formula I in which R represents an azaheterocyclic radical accessible to N-oxidation, for example pyridyl, can be converted by means of N-oxidation into compounds of the formula I in which R represents an N-oxidised azaheterocycle, for example N-oxidopyridyl.

The oxidation can be carried out in a manner known per se, for example by treatment with organic peracids, such as lower alkane peracids or arene peracids, such as optionally suitably substituted perbenzoic acids, for example peracetic or 3-chloroperbenzoic acid, preferably at room temperature or a slightly higher reaction temperature, or by treatment with aqueous hydrogen peroxide, for example at temperatures of up to 100° C., in the presence or absence of lower alkanoic acids, for example acetic acid. Care must be taken, especially when using peracids, to avoid over-oxidation resulting from an excessive reaction time.

Depending on the reaction conditions, compounds of the formula I can be obtained in free form or in the form of salts.

For example, resulting acid addition salts can be converted in a manner known per se, for example by treatment with a base, such as an alkali metal hydroxide, into the free compounds, or, for example, by treatment with suitable acids or derivatives thereof into other salts. Resulting free compounds of the formula I can be converted into their salts, for example by treatment with acids or corresponding anion exchangers.

Owing to the close relationship between the compounds of the formula I in free form and in the form of salts, hereinbefore and hereinafter there are to be understood by the free compounds of their salts optionally also the corresponding salts or free compounds, respectively, where appropriate with regard to meaning and purpose.

The compounds of the formula I, including the salts thereof, can also be obtained in the form of their hydrates, or their crystal may include, for example, the solvent used for the crystallisation.

Depending on the process reaction and/or the nature of the starting materials, the compounds of the formula I can be obtained in the form of mixtures of racemates, racemates or optical antipodes.

Resulting mixtures of racemates can be separated in a manner known per se, on the basis of the chemical structure and the physicochemical differences between the racemates, into the pure racemates or diastereoisomers, for example by chromatography and/or fractional crystallisation.

Racemates can be resolved into the optical antipodes according to methods that are known per se, for example by recrystallisation from an optically active solvent, with the aid of suitable microorganisms, or by reacting a compound of the formula I having salt-forming, for example basic, properties with an optically active salt-forming agent, such as an optically active acid, and separating the mixtures of salts obtained in this manner, for example on the basis of their different solubilities, into the diastereoisomeric salts, from which the antipodes can be freed, for example by treatment with a base.

Optical antipodes of neutral compounds of the formula I can be obtained, for example, also according to process (c) using an optically active acid of the formula V ($Ac^o$ represents carboxy, $Ac_1^o$ is esterified or amidated carboxy), and these are obtained, for example, from the corresponding racemic acid in customary manner, for example by salt formation with an optically active base, separation of the diastereoisomeric salts, and freeing of the optically active acid and conversion thereof into a compound containing the group $-COOR_1$ and corresponding to the formula I.

Further, for example, compounds of the formula I containing the group $-COOR_1$ can be transesterified using an optically active alcohol in accordance with the above-described process, and the resulting diastereoisomeric mixture can be resolved into the antipodes, for example by means of fractional crystallisation.

Advantageously, the pharmacologically more active diastereoisomer or the more active antipode is isolated from a diastereoisomeric mixture or racemate, respectively.

The invention relates also to those embodiments of the process according to which a compound obtainable as intermediate at any stage of the process is used as starting material and the remaining steps are carried out, or a starting material is used in the form of a derivative, for example a salt, and/or in the form of its racemates or antipodes, or is formed under the reaction conditions.

The starting materials used in the processes of the present invention are preferably those that result in the compounds described at the beginning as being especially valuable. The present invention relates also to novel starting materials and intermediates and to processes for the manufacture thereof.

The invention relates furthermore to the use of the compounds of the formula I or pharmaceutically acceptable salts of such compounds having salt-forming properties, especially as pharmacologically active compounds, especially as coronary dilators and antihypertensives for the treatment of cardiovascular pathological conditions, such as *Angina pectoris* and its sequelae, vascular spasms, central and peripheral circulatory disorders, high blood pressure, arrhythmiae and cardiac insufficiency, and also migraine, and also for the inhibition of platelet aggregation. They may be used, preferably in the form of pharmaceutical preparations, in a method for the prophylactic and/or therapeutic treatment of the human or animal body, especially for the treatment of cardiovascular pathological conditions, such as *Angina pectoris* and its sequelae, vascular spasms, high blood pressure and cardiac insufficiency.

The dosage of the active ingredient, which is administered on its own or together with the customary carrier and adjunct material, depends on the species to be treated, the age and individual condition, and on the method of administration. Depending on the nature of the disease, individual condition and age, the daily doses, for example for mammals with a body weight of approximately 70 kg, are preferably approximately from 10 to 500 mg, especially from approximately 20 mg to approximately 200 mg, and specifically approximately from 70 mg to 150 mg in the case of oral administration.

The invention relates furthermore to pharmaceutical preparations that contain compounds of the formula I or pharmaceutically acceptable salts of such compounds having salt-forming properties as active ingredients, to processes for their manufacture and to the use of compounds of the formula I or pharmaceutically acceptable salts thereof for the manufacture of medicaments, as coronary dilators and anti-hypertensives for the treatment of cardiovascular pathological conditions, such as *Angina pectoris* and its sequelae, vascular spasms, central and peripheral circulatory disorders, high blood pressure, arrhythmiae and cardiac insufficiency, and of migraine, and also for use as inhibitors in platelet aggregation.

The pharmaceutical preparations according to the invention are those for enteral, such as peroral or rectal administration, further for sublingual administration, and also for parenteral administration to warm-blooded animals. Corresponding dosage unit forms, especially for peroral and/or sublingual administration, for example dragées, tablets or capsules, contain preferably from approximately 10 mg to approximately 300 mg, especially from approximately 20 mg to approximately 200 mg, of a compound of the formula I or a pharmaceutically acceptable salt of a corresponding compound capable of salt-formation, together with pharmaceutically acceptable carriers.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatine, tragacanth, methylcellulose and/or, if desired, disintegrating agents, such as the mentioned starches, and also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores may be provided with suitable coatings that may be resistant to gastric juices, there being used, inter alia, concentrated sugar solutions optionally containing gum arabic, talc, polyvinylpyrrolidone, polyethylene glycol and/or titanium dioxide, lacquer solutions in suitable organic solvents or solvent mixtures or, for the manufacture of coatings that are resistant to gastric juices, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Other orally administrable pharmaceutical preparations are dry-fill capsules consisting of gelatine, and also sott sealed capsules consisting of gelatine and a plasticiser, such as glycerin or sorbitol. The dry-fill capsules may contain the active ingredient in the form of a granulate, for example in admixture with fillers, such as lactose, binders, such as starches, and/or glidants, such as talc or magnesium stearate, and, optionally, stabilisers. In soft capsules, the active ingredient is preferably dissolved or suspended in suitable liquids, such as fatty oils, paraffin oil or liquid polyethylene glycols, it also being possible to add stabilisers. Preferred are, inter alia, capsules that can either be bitten through easily, in order to achieve action as quickly as possible by sublingual absorption, or swallowed without being chewed.

Rectally administrable pharmaceutical preparations that come into consideration are, for example, suppositories which consist of a combination of the active ingredient and a suppository base material. Suitable suppository base materials are, for example, natural or synthetic triglycerides, paraffin hydrocarbons, polyethylene glycols or higher alkanols. It is also possible to use gelatine rectal capsules that contain a combination of the active ingredient with a base material. Suitable base materials are, for example, liquid triglycerides, polyethylene glycols or paraffin hydrocarbons.

Especially suitable for parenteral administration are aqueous solutions of an active ingredient in water-soluble form, for example in the formoof a water-soluble salt, and also suspensions of the active ingredient, such as corresponding oily injection suspensions, with suitable lipophilic solvents or vehicles, such as fatty oils, for example sesame oil, or synthetic fatty acid esters, for example ethyl oleate, or triglycerides, being used, or aqueous injection suspensions containing substances that increase the viscosity, for example sodium carboxymethylcellulose, sorbitol and/or dextran, and, optionally, stabilisers.

The pharmaceutical preparations of the present invention can be manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture, and processing the mixture or granulate, if desired or necessary, after the additin of suitable adjuncts, to form tablets or dragée cores.

The following Examples illustrate the invention described above; they are not intended, however, to limit the scope thereof in any way. Temperatures are given in degrees Celcius.

EXAMPLE 1

A solution of 6.2 g of 2,6-dimethyl-4-(3-nitrophenyl)-1,4-dihydropyridine-3,5-dicarboxlyic acid 3-methyl ester 5-[2-[N-(4-ethylenedioxy-4-(4-fluorophenyl)-n-butyl)-N-methylamino]ethyl ester] in 100 ml of 2N hydrochloric acid and 50 ml of ethanol is heated under reflux for 5 hours and the reaction solution is then concentrated in vacuo. Sodium hydroxide solution is added to the residue until a strongly alkaline reaction occurs, and the reaction mixture is extracted with methylene chloride. The organic phase is dried over sodium sulphate and evaporated to dryness and the residue is chromatographed on 300 times the amount of silica gel to yield 2,6-dimethyl-4-(3-nitrophenyl)-1,4-dihydropyridine-3,5-dicarboxylic acid 3-methyl ester 5-[2-[N-(4-(4-fluorophenyl)-4-oxo-n-butyl)-N-methylamino]ethyl ester] of the following formula

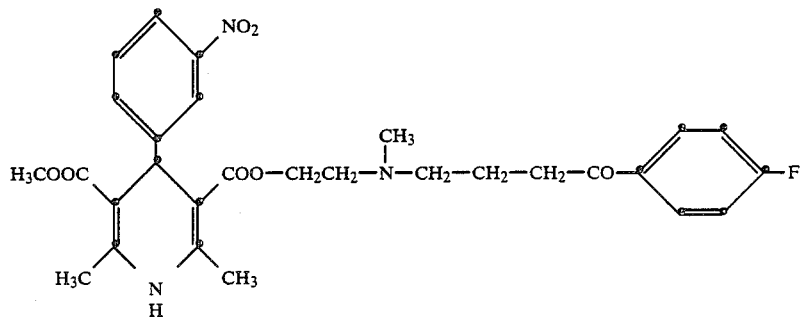

It has the following characteristics:
250 MHz FT-$^1$H-NMR (CDCl$_3$): 1.88 (m, 2H, —C—CH$_2$—C—); 2.24 (s, 3H, NCH$_3$); 2.36 (s, 6H, dihydropyridyl-CH$_3$); 2.44, 2.60 (2t, 4H, N—CH$_2$); 2.96 (t, 2H, —CH$_2$CO) 3.64 (s, 3H, COOCH$_3$); 4.12 (m, 2H, —OCH$_2$); 5.12 (s, 1H, 4-dihydropyridyl-H); 5.8 (s, 1H, NH); 7.1–8.15 (m, 8H, phenyl-H).

The starting material can be manufactured as follows:
A mixture of 4 g of 2,6-dimethyl-4-(3-nitrophenyl)-1,4-dihydropyridine-3,5-dicarboxylic acid 3-methyl ester 5-(2-chloroethyl ester) (DOS 2,407,115), 2.42 g of 2-(4-fluorophenyl)-2-[3-methylaminopropyl-(1)]-1,3dioxolane and 1.44 g of Hünig base is heated for 90 minutes, while stirring, in an oil bath preheated to 140°–150° C. After cooling, the solidified melt is taken up in ethyl acetate, and the organic phase is washed repeatedly with saturated sodium chloride solution then with water, dried over sodium sulphate and concentrated by evaporation to yield 2,6-dimethyl-4-(3-nitrophenyl)-1,4-dihydropyridine-3,5-dicarboxylic acid 3-methyl ester 5-[2-[N-(4-ethylenedioxy-4-(4-fluorophenyl)-n-butyl)-N-methylamino]ethyl ester], in the form of a crude product, which is further processed as such.

EXAMPLE 2

Analogously to the processes described in the description and to the process illustrated in the preceding Example it is possible, starting from corrsponding starting materials or, if they have salt-forming properties also from salts thereof, also to produce the followings compounds of the formula I or, if these have salt-forming properties, also salts thereof, especially pharmaceutically acceptable non-toxic acid addition salts thereof:

(a) 2,6-dimethyl-4-(3-nitrophenyl)-1,4-dihydropyridine-3,5-dicarboxylic acid 3-methyl ester 5-[2-[N-(4-(4-fluorophenyl)-1,4-dioxo-n-butyl)-N-methylamino]ethyl ester].

(b) 2,6-dimethyl-4-(3-nitrophenyl)-1,4-dihydropyridine-3,5-dicarboxylic acid 3-methyl ester 5-[2-[N-ethyl-N-(4-(4-fluorophenyl)-4-oxo-n-butyl)amino]ethyl ester].

(c) 2,6-dimethyl-4-(3-nitrophenyl)-1,4-dihydropyridine-3,5-dicarboxylic acid 3-methyl ester 5-[2-[N-benzyl-N-(4-(4-fluorophenyl)-4-oxo-n-butyl)amino]ethyl ester].

(d) 2,6-dimethyl-4-(3-nitrophenyl)-1,4-dihydropyridine-3,5-dicarboxylic acid 3-methyl ester 5-[2-[N-methyl-N-(4-phenyl-1,4-dioxo-n-butyl)amino]ethyl ester].

(e) 2,6-dimethyl-4-(3-nitrophenyl)-1,4-dihydropyridine-3,5-dicarboxylic acid 3-methyl ester 5-[2-[N-methyl-N-(4-phenyl-4-oxo-n-butyl)amino]ethyl ester].

(f) 2,6-dimethyl-4-(3-nitrophenyl)-1,4-dihydropyridine-3,5-dicarboxylic acid 3-methyl ester 5-[2-[N-benzyl-N-(4-phenyl-4-oxo-n-butyl)amino]ethyl ester].

(g) 2,6-dimethyl-4-(3-nitrophenyl)-1,4-dihydropyridine-3,5-dicarboxylic acid 3-methyl ester 5-[2-[N-methyl-N-(3-(2-thenoyl)propyl)amino]ethyl ester].

(h) 2,6-dimethyl-4-(3-nitrophenyl)-1,4-dihydropyridine-3,5-dicarboxylic acid 3-methyl ester 5-[2-[N-benzyl-N-(3-(2-thenoyl)propyl)amino]ethyl ester].

EXAMPLE 3

0.778 g of 2,6-dimethyl-4-(3-nitrophneyl)-1,4-dihydropyridine-3,5-dicarboxylic acid 3-methyl ester 5-(2-methylamino)ethyl ester (Chem. Pharm. Bull. 28, 2605, 1980), 0.401 g of ω-chloro-4-fluorobutyrophenone, 0.414 g of potassium carbonate and 0.3 g (0.002 mol) of sodium iodide are heated under reflux for 60 hours in 20 ml of isopropanol. The whole is then concentrated by evaporation in vacuo and sodium hydroxide solution is added to the residue until an alkaline reaction occurs; the reaction mixture is extracted with methylene chloride and the methylene chloride solution is subsequently washed with aqueous sodium thiosulphate solution. The organic phase is dried over sodium sulphate and then concentrated to dryness by evaporation. The residue is chromatographed on 300 times the amount of silica gel. In this manner 2,6-dimethyl-4-(3-nitrophenyl)-1,4-dihydropyridine-3,5dicarboxylic acid 3-methyl ester 5-[2-[N-(4-(4-fluorophenyl)-4-oxo-n-butyl)-N-methylamino]ethyl ester] is obtained; for characteristics see Example 1.

EXAMPLE 4

A mixture of 3.55 g of oxalyl chloride and 25 ml of acetonitrile is added dropwise to a mixture of 47 ml of dimethylformamide and 44 ml of acetonitrile over a period of 20 minutes at −30° C. while stirring. The white suspension is stirred for 30 minutes at −30° C., then 13.5 g of 2,6-dimethyl-4-(3-nitrophenyl)-1,4-dihydropyridine-3,5-dicarboxylic acid 3-methyl ester are added. The whole is further stirred until a yellow solution is formed. Then, at −30° C., a solution of 11.7 g of a mixture of N-4-(4-fluorophenyl)-4-oxo-n-butyl-N-methyl-2-amino-1-phenyl-ethanol and N-4-(fluorophenyl)-4-oxo-n-butyl-N-methyl-2-amino-2-phenyl-ethanol in 25 ml of pyridine is added dropwise. The whole is stirred overnight at room temperature to complete the reaction and then concentrated by evaporation under reduced pressure. The residue is dissolved in methylene chloride and extracted with water and soda. The organic phase is dried over sodium sulphate, concentrated and the residue is repeatedly chromatographed in a mixture of methylene chloride/methanol 98:2. In this manner 2,6-dimethyl-4-(3-nitrophenyl)-1,4-dihydropyridine-3,5-dicarboxylic acid 3-methyl ester 5-[2-[N-(4-(4-fluorophenyl)-4-oxo-n-butyl)-N-methylamino]-2-phenyl-ethyl ester] is obtained in amorphous form.

$^{13}$C-NMR (CDCl$_3$) (only the aliphatic carbon atoms of the side chain are indicated): 66.7, 66.6 (NCH); 64.2, 64.0 (OCH$_2$); 53.5, 53.4 (NCH$_2$); 51.11, 51.08 (OCH$_3$); 38.4 (NCH$_3$); 35.8 (CH$_2$CO); 21.7 (CH$_2$CH$_2$CO); R$_f$: 0.41 (methylene chloride/methanol: 95/5). 2,6-dimethyl-4-(3-nitrophenyl)-1,4-dihydropyridine-3,5-dicarboxylic acid 3-methyl ester 5-[2-[N-(4-(4-fluorophenyl)-4-oxo-n-butyl)-N-methylamino]-1-phenyl-ethyl ester] can be isolated in amorphous form from the same mixture. $^{13}$C-NMR (CDCl$_3$) (only the aliphatic carbon atoms of the side chain are indicated): 73.3 (d, OCH); 62.7 (t, NCH$_2$CH); 56.6 (t, NCH$_2$CH$_2$); 42.5 (q, NCH$_3$); 35.9 (t, CH$_2$CO); 21.5 (t, CH$_2$CH$_2$CO); R$_f$: 0.38 (methylene chloride/methanol: 95/5).

The starting materials can be manufactured as follows:

2,6-dimethyl-4-(3-nitrophenyl)-1,4-dihydropyridine-3,5-dicarboxylic acid 3-methyl ester is described in EP-A-No. 11706 (Bayer).

For the manufacture of the amino alcohols, a mixture of 20 g of 2-(3-chloropropyl)-2-(4-fluorophenyl)-1,3-dioxolane, 9.9 g of N-benzylmethylamine and 22.5 g of potassium carbonate in 50 ml of acetone is heated under reflux for 3 days. The whole is then filtered, the filtrate is concentrated by evaporation and the residue is purified by flash chromatography using a mixture of methylene chloride/methanol (98:2). The resulting aminodioxolane is debenzylated in alcohol with Pd/C at room temperature.

A mixture of 4.8 g of the resulting 2-(3-methylaminopropyl)-2-(4-fluorophenyl)-1,3-dioxolane with 2.9 g of phenylethylene oxide is heated under reflux for 15 hours in 50 ml of isopropanol. After concentration by evaporation, the residue is purified by flash chromatography using a mixture of methylene chloride/methanol (98:2). The mixture of the resulting ketalised amino alcohols is further processed directly.

6.0 g of the ketalised amino alcohol mixture are heated under reflux for 4 hours with 100 ml of 2N HCl and 150 ml of acetone. The solution is concentrated by evaporation and the residue is partitioned between methylene chloride and water. The aqueous solution is rendered alkaline with sodium bicarbonate and extracted with methylene chloride. The organic phase is dried and concentrated by evaporation. The mixture of N-4-(4-fluorophenyl)-4-oxo-n-butyl-N-methyl-2-amino-1-phenylethanol and N-4-(4-fluorophenyl)-4-oxo-n-butyl-N-methyl-2-amino-2-phenylethanol is directly esterified with the dihydropyridinecarboxylic acid.

EXAMPLE 5

Tablets each containing 20 mg of active ingredient are manufactured in customary manner with the following composition:

| Composition: | |
|---|---|
| 2,6-dimethyl-4-(3-nitrophenyl)-1,4-dihydropyridine-3,5-dicarboxylic acid 3-methyl ester 5-[2-[N—(4-(4-fluorophenyl)-4-oxo-n-butyl)-N—methylamino]-ethyl ester] | 20 mg |
| wheat starch | 60 mg |
| lactose | 50 mg |
| colloidal silica | 5 mg |
| talc | 9 mg |
| magnesium stearate | 1 mg |
| | 145 mg |

Manufacture:

The active ingredient is mixed with a portion of the wheat starch, with the lactose and with the colloidal silica and the mixture is forced through a sieve. A further portion of the wheat starch is made into a paste with 5 times the amount of water on a water bath and the powder mixture is kneaded with this paste until a slightly plastic mass is formed. The plastic mass is pressed through a sieve having a mesh width of approximately 3 mm, dried, and the resulting dry granulate is again forced through a sieve. Then, the remaining wheat starch, the talc and the magnesium stearate are admixed and the mixture is compressed to form 145 mg tablets with a breaking notch.

EXAMPLE 6

Capsules containing 10 mg of active ingredient are manufactured in customary manner as follows:

| Composition: | |
|---|---|
| 2,6-dimethyl-4-(3-nitrophenyl)-1,4-dihydropyridine-3,5-dicarboxylic acid 3-methyl ester 5-[2-[N—(4-(4-fluorophenyl)-4-oxo-n-butyl)-N—methylamino]-ethyl ester] | 2500 mg |
| talc | 200 mg |
| colloidal silica | 50 mg |

Manufacture:

The active ingredient is intimately mixed with the talc and colloidal silica, the mixture is forced through a sieve having a mesh width of 0.5 mm, and hard gelatine capsules of suitable size are each filled with an 11 mg portion of this mixture.

EXAMPLE 7

A solution of 5.0 g of 2,6-dimethyl-4-(3-nitrophenyl)-1,4-dihydropyridine-3,5-dicarboxylic acid 3-methyl ester 5-[2-[N-(4-(4-fluorophenyl)-4-oxo-n-butyl)-N-methylamino]ethyl ester] in 9 ml of 1N hydrochloric acid is made up to 5000 ml with water. The sterile solution is filled into 5 ml ampoules that contain 5 mg of active ingredient in 5 ml of solution.

EXAMPLE 8

Instead of the compounds used as active ingredient in Examples 5 to 7 it is also possible to use as active ingredients in tablets, dragées, capsules etc. the compounds of the formula I mentioned in Examples 2 and 4 or, if they have salt-forming properties, the pharmaceutically acceptable non-toxic acid addition salts thereof.

We claim:

1. A compound of the formula:

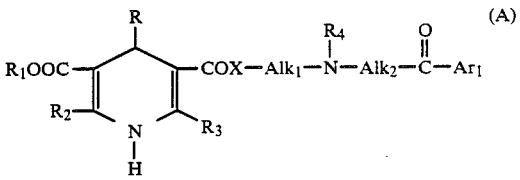

wherein R is phenyl substituted by 1 to 2 substituents selected from the group consisting of nitro, cyano, carbonyl, lower-alkoxy carbonyl and carbamyl;
Ar$_1$ is halophenyl;
R$_1$, R$_2$ and R$_3$ are each independently lower alkyl;
R$_4$ is hydrogen, lower alkyl or benzyl;
X is oxygen;
Alk$_1$ is
 (a) (CH$_2$)$_n$ in which n is 2–6 or
 (b) —(CH$_2$)$_{n1}$ which is substituted by phenyl, which phenyl is itself unsubstituted or substituted by a substituent selected from lower alkyl, hydroxy, lower alkoxy, halo-lower alkoxy, halogen, carboxy, lower alkoxyarbonyl, and cyano, and n1 is 2–4;
Alk$_2$ is (CH)$_m$ in which m is 2–6 or a pharmaceutically acceptable acid addition salt thereof.

2. A compound or pharmaceutically acceptable acid addition salt thereof according to claim 1 wherein R$_4$ is hydrogen or lower alkyl.

3. A compound or pharmaceutically acceptable acid addition salt thereof according to claim 1 wherein Alk$_1$ is —(CH$_2$)$_n$ and n is 2–4.

4. A compound or pharmaceutically acceptable acid addition salt thereof according to claim 1 wherein Alk$_2$ is —(CH$_2$)$_m$ and m is 2–4.

5. A compound or pharmaceutically acceptable acid addition salt thereof according to claim 1 wherein Ar$_1$ represents phenyl which is substituted by halogen having an atomic number of up to and including 35.

6. A compound or pharmaceutically acceptable acid addition salt thereof according to claim 1 wherein Alk$_1$ and Alk$_2$ each represents the group —(CH$_2$)$_n$ wherein n represents an integer of 2 or 3.

7. A compound or pharmaceutically acceptable acid addition salt thereof according to claim 1 wherein R$_4$ represents lower alkyl.

8. A compound or pharmaceutically acceptable acid addition salt thereof according to claim 1 wherein R represents phenyl that is mono- or di-substituted in the 2- or 3-position by nitro or cyano.

9. A compound or pharmaceutically acceptable acid addition salt thereof according to claim 1 wherein
R$_1$, R$_2$ and R$_3$ each represents lower alkyl having up to 4 carbon atoms;
Alk$_1$ and Alk$_2$ each represents unsubstituted, α,ω-alkylene having 2 or 3 carbon atoms; and
Ar$_1$ represents phenyl mono-substituted by halogen having an atomic number of up to and including 35.

10. The compound or pharmaceutically acceptable acid addition salt thereof according to claim 1 in which
R represents phenyl that is mono-substituted by nitro or cyano, the subtituent occupying the 2 , or 3-, position,
Alk$_1$ and Alk$_2$ each represents the group —(CH$_2$)$_n$ wherein n represents an integer of 2 or 3,
R$_4$ represents lower alkyl, and Ar₁ represents phenyl substituted by halogen having an atomic number of up to and including 35.

11. The compound or pharmaceutically acceptable acid addition salt thereof according to claim 1 in which
R represents phenyl that is mono-substituted in the 2- or 3-position by nitro or cyano,
R₁, R₂ and R₃ each represents lower alkyl having up to 4 carbon atoms,
Alk₁ represents, α,ω-alkylene having 2 or 3 carbon atoms,
Alk₂ represents, α,ω-alkylene having 2 or 3 carbon atoms,
R₄ represents lower alkyl having up to 4 carbon atoms that is unsubstituted or is substituted by phenyl, and
Ar₁ represents phenyl which is substituted by halogen having an atomic number of up to and including 35.

12. A compound selected from 2,6-dimethyl-4-(3-nitrophenyl)-1,4-dihydropyridine-3,5-dicarboxylic acid 3-methyl ester 5-[2-[N-ethyl-N-(4-(4-fluorophenyl)-4-oxo-n-butyl)amino)ethyl ester], 2,6-dimethyl-4-(3-nitrophenyl)--1,4-dihydropyridine-3,5-dicarboxylic acid 3-methyl ester 5-[2-[N-benzyl-N-(4-(4-fluorophenyl)-4-oxo-n-butyl)amino]ethyl ester], or a pharmaceutically acceptable acid addition salt thereof.

13. The compoud claimed in claim 1 being 2,6-dimethyl-4-(3-nitrophenyl)-1,4-dihydropyridine-3,5-dicarboxylic acid 3-methyl ester 5-[2-[N-(4-(4-fluoorophenyl)-4-oxo-n-butyl)-N-methyl-amino]ethyl ester] or a pharmaceutically acceptable acid addition salt thereof.

14. The compound claimed in claim 1 being 2,6-dimethyl-4-(3-nitrophenyl)-1,4-dihydropyridine-3,5-dicarboxylic acid 3-methyl ester 5-[2-[N-(4-(4-fluorophenyl)-4-oxo-n-butyl)-N-methylamino]-2-phenylethyl ester], or a pharmaceutically acceptable acid addition salt thereof.

15. The compound claimed in claim 1 being 2,6-dimethyl-4-(3-nitrophenyl)-1,4-dihydropyridine-3,5-dicarboxylic acid 3-methyl ester 5-[2-[N-(4-(4-fluorophenyl)-4-oxo-n-butyl)-N-methyl-amino]-1-phenylethyl ester] or a pharmaceutically acceptable acid addition salt thereof.

16. A pharmaceutical composition comprising a therapeutically effective amount of a compound or pharmaceutically acceptable acid addition salt thereof of claim 4 and a pharmaceutically acceptable excipient or carrier.

17. A method for the treatment of cardiovascular pathological conditions, selected from the group consisting of *Angina pectoris* and its sequelae, vascular spasms, central and preipheral circulatory disorders, high blood pressure, arrhythmiae and cardiac insufficiency, in a patient in need thereof comprising administering to said patient a pharmaceutically effective amount of a compound claimed in claim 1 or a pharmaceutically acceptable acid addition salt thereof.

18. A method for the treatment of migraine, in a patient in need thereof comprising administering to said patient a pharmaceutically effective amount of a compound of claim 1 or a pharmaceutically acceptable acid addition salt thereof.

19. A method for the treatment of platelet aggregation in a patient in need thereof comprising administering to said patient a pharmaceutically effective amount of a compound of claim 1 or a pharmaceutically acceptable acid addition salt thereof.

* * * * *